United States Patent
Dunlop

(10) Patent No.: US 9,717,878 B2
(45) Date of Patent: Aug. 1, 2017

(54) METHOD AND APPARATUS FOR FACILITATING DELIVERY OF ANAESTHETIC

(71) Applicant: Colin Dunlop, East Ryde (AU)

(72) Inventor: Colin Dunlop, East Ryde (AU)

(*) Notice: Subject to any disclaimer, the term of this patent is extended or adjusted under 35 U.S.C. 154(b) by 326 days.

(21) Appl. No.: 14/280,258

(22) Filed: May 16, 2014

(65) Prior Publication Data

US 2015/0013676 A1    Jan. 15, 2015

Related U.S. Application Data

(63) Continuation of application No. PCT/AU2012/001428, filed on Nov. 19, 2012.

(30) Foreign Application Priority Data

Nov. 18, 2011  (AU) ................................ 2011904836

(51) Int. Cl.
*A61M 16/12*    (2006.01)
*A61M 16/01*    (2006.01)
(Continued)

(52) U.S. Cl.
CPC ...... *A61M 16/127* (2014.02); *A61M 16/0045* (2013.01); *A61M 16/01* (2013.01);
(Continued)

(58) Field of Classification Search
CPC .............. A61M 16/00; A61M 16/0078; A61M 16/009; A61M 16/01; A61M 16/08;
(Continued)

(56) References Cited

U.S. PATENT DOCUMENTS 2,617,414 A    11/1952 Hollmann
3,707,965 A    1/1973 Guzay
(Continued)

FOREIGN PATENT DOCUMENTS

CA    2326822 A1    5/2001
EP    0823627 A1    2/1998
(Continued)

OTHER PUBLICATIONS

International Search Report dated Jan. 16, 2013, issued in International Application No. PCT/AU2012/001428, filed Nov. 19, 2012.
(Continued)

*Primary Examiner* — Annette Dixon
(74) *Attorney, Agent, or Firm* — Knobbe Martens Olson & Bear, LLP

(57) ABSTRACT

The present invention relates to a method and apparatus for facilitating anaesthesia, particularly in Re-Breather anaesthetic circuits. A problem with Re-Breather circuits is that their dynamic response can be relatively slow. The dynamic response is the response of the circuit to delivering changes of anaesthetic concentration. In current circuits, Fresh Gas containing anaesthetic is delivered into the circuit and may be substantially diluted by the gas already present in the circuit. It is therefore difficult to achieve a rapid increase of anaesthetic concentration for delivery to the patient. In the present invention, an accumulator is placed in the Re-Breather circuit to accumulate Fresh Gas containing anaesthetic as it is introduced into the circuit, adjacent an inhalation conduit to the patient. Fresh Gas containing high concentrations of anaesthetic is therefore immediately available to the patient.

19 Claims, 19 Drawing Sheets

(51) Int. Cl.
*A61M 16/22* (2006.01)
*A61M 16/08* (2006.01)
*A61M 16/10* (2006.01)
*A61M 16/20* (2006.01)
*A61M 16/00* (2006.01)
*A61M 16/18* (2006.01)

(52) U.S. Cl.
CPC ...... *A61M 16/0891* (2014.02); *A61M 16/104* (2013.01); *A61M 16/1095* (2014.02); *A61M 16/12* (2013.01); *A61M 16/209* (2014.02); *A61M 16/22* (2013.01); *A61M 16/0051* (2013.01); *A61M 16/0078* (2013.01); *A61M 16/18* (2013.01); *A61M 2016/0036* (2013.01); *A61M 2202/0208* (2013.01); *A61M 2202/0241* (2013.01); *A61M 2202/0275* (2013.01); *A61M 2205/3317* (2013.01); *A61M 2205/3368* (2013.01); *A61M 2230/432* (2013.01)

(58) Field of Classification Search
CPC ............ A61M 16/0808; A61M 16/085; A61M 16/1015; A61M 16/104; A61M 16/12; A61M 16/18; A61M 16/204; A61M 16/22; A61M 2016/1025; A61M 2016/1035; A61M 2205/12; A61M 2205/6063; A61M 2230/005; A61M 2230/205; A61M 2230/437; A62B 19/00; F16L 55/04; Y02C 10/06; Y02C 20/10; Y10S 128/909; Y10S 128/91; Y10S 128/911; Y10S 128/912; Y10S 55/33; Y10T 137/2499
USPC ............ 128/200.11, 202.22, 202.27, 203.12, 128/203.14, 203.28, 204.13, 204.14, 128/204.15, 204.16, 204.21, 204.22, 128/204.23, 205.11, 205.12, 205.15, 128/205.17, 205.23, 205.28, 909, 910, 128/911, 912
See application file for complete search history.

(56) References Cited

U.S. PATENT DOCUMENTS

| | | | | |
|---|---|---|---|---|
| 3,794,027 | A * | 2/1974 | Johnson | A61M 16/18 128/204.13 |
| 4,127,121 | A * | 11/1978 | Westenskow | A61M 16/104 128/203.14 |
| 4,353,366 | A * | 10/1982 | Bickford | A61M 16/22 128/205.12 |
| 4,602,653 | A | 7/1986 | Ruiz-Vela et al. | |
| 6,948,493 | B2 * | 9/2005 | Dunlop | A61M 16/08 128/200.11 |
| 7,997,268 | B1 | 8/2011 | Leonard et al. | |

FOREIGN PATENT DOCUMENTS

| | | |
|---|---|---|
| EP | 1048312 A2 | 11/2000 |
| GB | 1008520 A | 10/1965 |
| GB | 2338902 A | 1/2000 |
| JP | 0715538 A | 6/1995 |
| WO | WO 01/00236 A2 | 1/2001 |
| WO | WO 2011/014908 A1 | 2/2011 |

OTHER PUBLICATIONS

International Preliminary Report on Patentability dated Feb. 26, 2014, issued in International Application No. PCT/AU2012/001428, filed Nov. 19, 2012.
Extended European Search Report dated Mar. 5, 2015 in corresponding European Application No. 12848779.0.

* cited by examiner

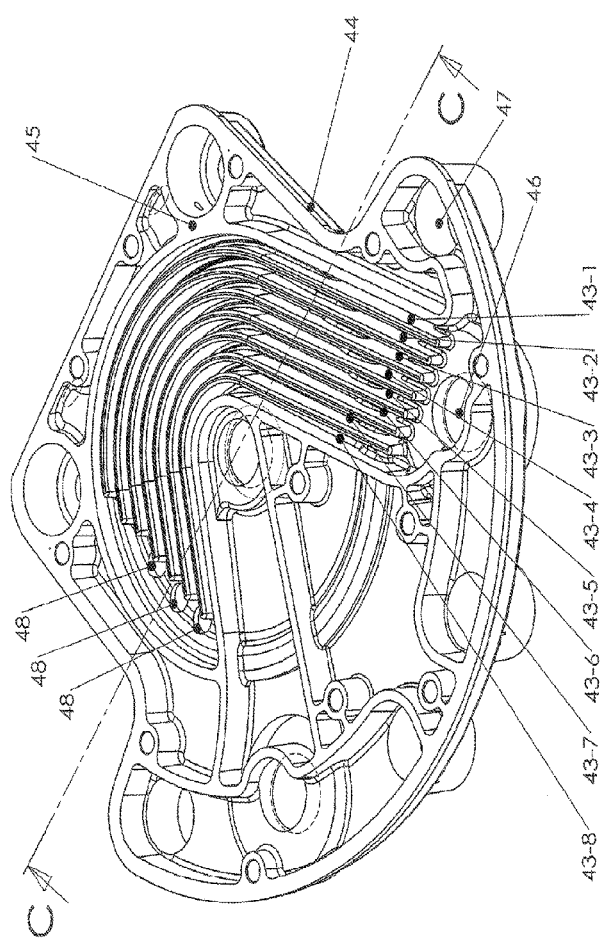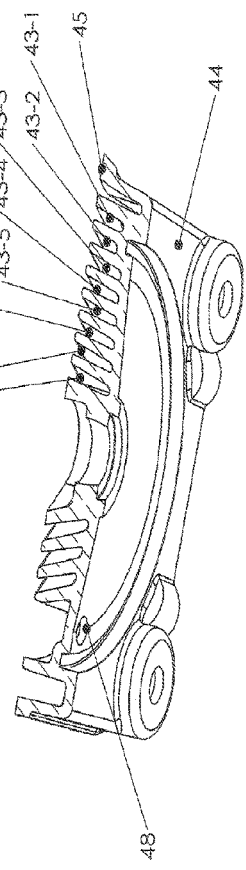
Figure 11
Figure 12

METHOD AND APPARATUS FOR FACILITATING DELIVERY OF ANAESTHETIC

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation, under 35 U.S.C. §120, of International Patent Application No. PCT/AU2012/001428, filed on Nov. 19, 2012 under the Patent Cooperation Treaty (PCT), which was published by the International Bureau in English on May 23, 2013, which designates the United States, which claims benefit to priority of Australian Patent Application No. 2011904836 filed on Nov. 18, 2011, the disclosures of which are hereby expressly incorporated by reference in their entirety and are hereby expressly made a portion of this application.

FIELD OF THE INVENTION

The present invention relates to a method and apparatus for facilitating anaesthesia and, particularly, but not exclusively, relates to a method and apparatus of facilitating anaesthesia in a Re-Breather anaesthetic circuit.

BACKGROUND OF THE INVENTION

So-called "Re-Breather circuits" (otherwise known as "circle systems") are well known anaesthetic circuits for delivering anaesthetic to patients.

Anaesthetic circuits deliver a mixture of oxygen ($O_2$) and anaesthetic to a patient. A Re-Breather circuit recycles unused $O_2$ and anaesthetic and removes unwanted carbon dioxide exhaled by the patient.

Re-Breather circuits are widely used, and their operation well understood. A typical Re-Breather circuit is supplied by Fresh Gas (a mixture of $O_2$ and anaesthetic) from a vaporiser. The Re-Breather circuit includes two hoses and two one way valves which connect to the patient and enable the patient to first inhale $O_2$ and anaesthetic from the inhalation side of the circuit and to then exhale $CO_2$, and unused $O_2$ and anaesthetic back into the exhalation side of the circuit—thus ensuring a one way flow of gases through the hoses from the inhalation side to the exhalation side of the circuit.

The Re-Breather circuit additionally contains a soda lime canister filled with soda lime, a breather bag and a pressure relief valve. The exhaled gases pass through the soda lime where the $CO_2$ is absorbed before they are recycled back to the inhalation side of the circuit to be Re-Breathed by the patient. The breathing bag acts as a capacitor in the circuit to absorb or dampen the pressure fluctuations that would otherwise occur when the patient inhales and exhales.

The pressure relief valve has two functions. Firstly it ensures that the Re-Breather circuit and the patient attached to this circuit is not pressurised to a level that is dangerous to the patient. Secondly it maintains the mass of gases contained in the Re-Breather circuit approximately constant. In this respect the circuit is constantly fed with a mixture of new $O_2$ and anaesthetic (Fresh Gas) to provide replacement anaesthetic for that absorbed by the patient and replacement $O_2$ for that converted to $CO_2$ by the patient and subsequently absorbed by the soda lime. In order to maintain the mass of gases in the Re-Breather circuit approximately constant the pressure relief valve must release a mass equal to the mass of Fresh Gas delivered to the Re-Breather circuit minus the mass of $CO_2$ absorbed by the Soda Lime and the mass of anaesthetic gas absorbed by the patient.

There are a number of issues with Re-Breather circuits and they are not necessarily ideal for all types of patients.

One problem associated with Re-Breather circuits is a poor dynamic response to changes in patient demand for increased anaesthetic concentration. The need for rapid increase in the anaesthetic concentration of the patient typically occurs when the patient starts to wake up during an operation. Rapid increase in the anaesthetic concentration delivered to the patient is required if the patient is to be put back to sleep. Poor dynamic response (depending, in part, on patient type) can mean that the patient may not be put back to sleep in appropriate time, or receive the right amount of anaesthetic to keep them at the correct anaesthetic depth.

Re-Breather circuits also have a certain amount of resistance to breathing, which may not be suitable for all types of patients.

Although currently available Re-Breather circuits may perform satisfactorily to maintain anaesthetic depth of adult sized human patients e.g. 40 kg and over, there are issues with their use by smaller patients, particularly under 15 kgs. Re-Breather circuits are used in veterinary medicine as well as human medicine. Because of the difficulties with smaller patients, such, as small animals, and the impracticality of designing Re-Breather circuits particularly for smaller patients, typically small patients such as small animals are not anaesthetised using Re-Breather circuits. Instead, such patients are anaesthetised using "open circuits" (or "None Re-Breather circuits"). Open circuits are high-flow systems. Large amounts of anaesthetic, in the order of a liter per minute in some cases, are used. This is very expensive. Also, a significant amount of anaesthetic leaks into the surrounding environment from the open system, causing a potential health hazard. The active provision and removal of anaesthetic/gas mixture is therefore very wasteful and expensive. With open systems, it is also very difficult to ensure with any precision that a patient is anaesthetised. It is difficult to tell with any accuracy the concentration of anaesthetic gas mixture at the patient respiratory orifices. There will be, for example, entrainment of room air because of the open system, which can dilute the anaesthetic gas mixture. It can therefore be very difficult to maintain anaesthetic depth with open circuits.

SUMMARY OF THE INVENTION

In accordance with a first aspect, the present invention provides an anaesthetic apparatus, comprising a conservation arrangement, which is arranged to slow mixing of Fresh Gas entering an anaesthetic circuit, with gas already contained in the anaesthetic circuit.

In an embodiment, the conservation arrangement is arranged to store Fresh Gas entering the anaesthetic circuit in a manner that minimises the dilution of the Fresh Gas by the gas already resident in the anaesthetic circuit.

In an embodiment, the anaesthetic apparatus is a component arranged to fit to other components forming the anaesthetic circuit. The conservation arrangement may comprise one or more ports and passageways arranged to fit to other components of the anaesthetic circuit. In an embodiment, the anaesthetic circuit is a Re-Breather circuit. In embodiment, the anaesthetic apparatus may comprise the conservation arrangement and also further components of an anaesthetic circuit. Where the anaesthetic circuit is a Re-Breather circuit, the components may include ports and tubes, valves and other components, enabling implementation of the Re-Breather circuit.

In an embodiment, the anaesthetic circuit is arranged so that the Fresh Gas (which, in an embodiment, contains the anaesthetic) enters the anaesthetic circuit at or near an inhalation part of the anaesthetic circuit. Fresh Gas which is not substantially diluted by the gas already contained in the anaesthetic circuit, is therefore advantageously available near or at the inhalation part of the circuit. In an embodiment, the inhalation part of the circuit includes an inhalation conduit leading to a patient interface, such as a mask. The inhalation part of the circuit also includes the volume at the Fresh Gas inlet and downstream of the Fresh Gas inlet (towards the inhalation conduit).

In an embodiment, because undiluted or slightly diluted Fresh Gas is available at the inhalation part, the dynamic response of the anaesthetic circuit is better. For example, if it is wished to increase the anaesthetic dose to a patient by injecting Fresh Gas with more anaesthetic, the Fresh Gas with the new concentration of anaesthetic will be slower to dilute, will be available at the inhalation part, and therefore available to reach the patient with a higher anaesthetic dose quickly. Advantageously, the newly introduced Fresh Gas is conserved near the inhalation part for a longer time than would be the case in prior art systems. In prior art anaesthetic circuits, particularly Re-Breather circuits which have large volumes, Fresh Gas is quickly diluted with gas already contained in the anaesthetic circuit.

The dynamic response of an anaesthetic circuit incorporating an anaesthetic apparatus in accordance with this embodiment is advantageously improved. Improving the dynamic response advantageously enables anaesthetic circuit such as Re-Breather circuits, to be used with more efficiency and also to be used with smaller patients such as patients under 10 to 15 kgs.

As well as being advantageous for use with smaller patients, embodiments of the anaesthetic apparatus increase efficiency over conventional Re-Breather circuits and are useful for all sizes of human and animal patients. The dynamic response is improved for every type of patient. The system is therefore more efficient. Lower Fresh Gas flows may be used as compared with prior art circuits. This provides a saving in costs and reduces pollution.

In an embodiment, the conservation arrangement comprises an accumulator arranged to accumulate Fresh Gas entering the anaesthetic circuit. In an embodiment the accumulator has a geometry arranged to reduce mixing of the Fresh Gas with gas already in the anaesthetic circuit. In an embodiment, the accumulator comprises an accumulator passage of relatively small cross-sectional area compared with the rest of the anaesthetic circuit. In an embodiment, the accumulator passage has a cross-sectional area that is 50% or less than that of the minimum cross-sectional area of the rest of the anaesthetic circuit. In an embodiment, the accumulator comprises a plurality of accumulator passages arranged side by side. In an embodiment, the plurality of accumulator passages have a combined cross-sectional area which is 50% or less than that of the minimum cross-sectional area of the rest of the anaesthetic circuit. A proximal end of the accumulator is arranged to be positioned proximate a Fresh Gas inlet of the anaesthetic circuit and an inspiration arm of the anaesthetic circuit. In an embodiment, a distal end of the accumulator is arranged to be positioned proximate an expiration arm of the anaesthetic circuit. The accumulator acts to store and conserve Fresh Gas which is entering the anaesthetic circuit, and slow its dilution by gas already in the circuit.

In an embodiment, one or more other components of the anaesthetic circuit are positioned in the anaesthetic circuit to facilitate the slowing of the mixing of gas.

In an embodiment, components of the anaesthetic circuit may be designed to facilitate the slowing of the mixing of gas.

In an embodiment, the anaesthetic apparatus further comprises a canister arranged to contain carbon dioxide absorbent and comprising an outlet and an inlet, the outlet arranged to be positioned after the distal end of the accumulator. The inlet and outlet may be arranged so that gas flow through the canister is unidirectional from one end of the canister to the other, and from a central part of the canister to the outside of the canister. The outlet and inlet may be arranged to be positioned with respect to the anaesthetic apparatus such that the flow occurs downwardly from the inlet to the outlet, in use.

In an embodiment, the volume of the accumulator is arranged to be of the same order of magnitude as the tidal volume of the patient to be anaesthetised using the anaesthetic circuit. The volume of the accumulator may be in the range of 30 ml to 130 ml, in an embodiment in the range of 35 ml to 100 ml, in an embodiment in the range 40 ml to 70 ml and in a further embodiment in the range of 45 ml to 55 ml.

In an embodiment, the volume of the accumulator is equal to or greater than one quarter of the tidal volume of the smallest patient for which the anaesthetic circuit is to be used.

Another problem with the operation of conventional Re-Breather circuits, particularly with smaller patients, is the difficulty that smaller patients have operating the inhalation and exhalation valves (and other valves) in the circuit. Patients with a relatively small tidal volume, for example less than 50 ml, often have difficulty operating conventional valves in such circuits.

In an embodiment, the anaesthetic apparatus further comprises an inhalation valve and an exhalation valve, the inhalation valve and exhalation valve being arranged to be operated by patients having relatively low tidal volumes. The valves may comprise leaf valves, wherein the leaves comprise a flexible plastics material. In an embodiment, the leaves are of polypropylene, being in the order 0.1 mm to 1.5 mm in thickness, more particularly 0.8 to 1.2 mm, more particularly 1 mm.

In accordance with a second aspect, the present invention provides an anaesthetic apparatus, comprising a housing mounting a conservation arrangement, the housing comprising ports and passageways arranged to connect to other components in an anaesthetic circuit.

In an embodiment, the ports and passageways of the housing are arranged to connect to other components of the anaesthetic circuit at positions which optimise the operation of the conservation arrangement. In an embodiment, the ports and passageways comprise a pressure release valve port arranged to connect to a pressure release valve, whereby the pressure release valve port is, in operation, at a position in the anaesthetic circuit where the concentration of the anaesthetic is lowest.

In accordance with a third aspect, the present invention provides an anaesthetic apparatus component, comprising a canister arranged to contain a carbon dioxide absorbent, to absorb carbon dioxide in an anaesthetic circuit, the canister comprising an inlet and outlet arranged so that gas flow through the canister is unidirectional from end of the canister to the other.

In an embodiment, gas flow is from a central portion of the canister to the outside of the canister.

Advantageously, the canister efficiently utilises the carbon dioxide absorbent in operation.

In an embodiment, the canister outlet and inlet are arranged to be positioned with respect to the anaesthetic circuit, such that flow occurs downwardly from the inlet to the outlet.

In accordance with a fourth aspect, the present invention provides an anaesthetic apparatus comprising a valve, arranged to be used in an anaesthetic circuit, the valve being arranged to be operated by patients having relatively low tidal volumes.

In an embodiment, the tidal volume is less than 100 ml, in an embodiment less than 70 ml, in an embodiment less than 60 ml and in an embodiment less than 55 ml.

In an embodiment, the valve comprises a leaf valve and the leaf comprise a plastics material. The leaves may be of polypropylene, being between 0.1 mm and 1.5 mm in thickness. In an embodiment, the valve leaf is 1 mm thickness.

In accordance with a fifth aspect, the present provides an anaesthetic circuit comprising a plurality of components which are positioned within the anaesthetic circuit in order to slow mixing of Fresh Gas entering the circuit with gas already contained in the anaesthetic circuit.

In an embodiment, the anaesthetic circuit is a Re-Breather circuit.

In accordance with a sixth aspect, the present invention provides a method of facilitating anaesthesia, comprising the steps of slowing mixing of Fresh Gas entering an anaesthetic circuit with gas already contained in the anaesthetic circuit.

In an embodiment, the step of slowing mixing of Fresh Gas comprises a step of accumulating Fresh Gas entering the circuit.

In an embodiment, the step of accumulating the Fresh Gas comprises accumulating the Fresh Gas proximate an inhalation portion of the anaesthetic circuit, which may be an inspired limb of the anaesthetic circuit.

In an embodiment, the step of slowing mixing of the Fresh Gas, comprises positioning components of the anaesthetic circuit to facilitate the slowing.

In accordance with a seventh aspect, the present invention provides a method of facilitating anaesthesia, comprising the steps of conserving Fresh Gas entering the anaesthetic circuit, conserving the gas at a part of the circuit proximate an inhalation portion of the circuit.

In an embodiment, the step of conserving the Fresh Gas comprises the step of accumulating the Fresh Gas.

In accordance with an eighth aspect, the present invention provides an anaesthetic apparatus, comprising a damping arrangement, which is arranged to damp mixing of Fresh Gas entering an anaesthetic circuit, with gas already contained in the anaesthetic circuit.

The damping arrangement is arranged to damp the mixing of Fresh Gas with the gas already contained in the circuit, in the sense of checking or retarding the action of mixing, slowing down the mixing.

In an embodiment, the anaesthetic circuit is a Re-Breather circuit.

In an embodiment, the damping arrangement comprises a conservation arrangement arranged to conserve Fresh Gas in a part of the anaesthetic circuit.

In an embodiment, the damping arrangement comprises an accumulator arranged to accumulate the Fresh Gas in the part of the circuit and limit its mixing with anaesthetic gases in other parts of the anaesthetic circuit.

In other embodiments, the damping arrangement may comprise any other arrangement which slows the mixing of Fresh Gas with gas in other parts of the anaesthetic circuit. It may comprise a valve arrangement, for example, a constriction arrangement, or any other arrangement.

In accordance with a ninth aspect, the present invention provides an anaesthetic apparatus, arranged for implementation of an anaesthetic Re-Breather circuit, the anaesthetic apparatus comprising a housing, having a Fresh Gas port for receiving Fresh Gas from a vaporiser, an inhalation port for providing gas to an inhalation conduit for a patient, an exhalation port for receiving expired gas from a patient, the anaesthetic apparatus further comprising a container for containing carbon dioxide absorbent, and a compliant reservoir for absorbing pressure fluctuations within the anaesthetic circuit, the Fresh Gas port, inhalation port, exhalation port, carbon dioxide absorbent container and compliant reservoir being connected by passageways such that a circuit is formed through which gas flows in one direction from the Fresh Gas port, the inhalation port to the patient, from the exhalation port, to the canister and compliant reservoir and back to the inhalation port, wherein the Fresh Gas inlet and inhalation port are proximate one another and wherein the anaesthetic apparatus further comprises an accumulator located downstream of the inlet port and inhalation port, the accumulator being arranged to conserve Fresh Gas and slow mixing of the Fresh Gas with the gas in the rest of the circuit.

BRIEF DESCRIPTION OF THE DRAWINGS

Features and advantages of the present invention will become apparent from the following description of embodiments thereof, by way of the example only, with reference to the accompanying drawing in which:

FIG. 11 is a perspective view of internal components of an anaesthetic apparatus in accordance with a further embodiment of the present invention;

FIG. 12 is a sectional view of the apparatus of FIG. 11;

DETAILED OF THE DESCRIPTION OF EMBODIMENTS

Figure 17:
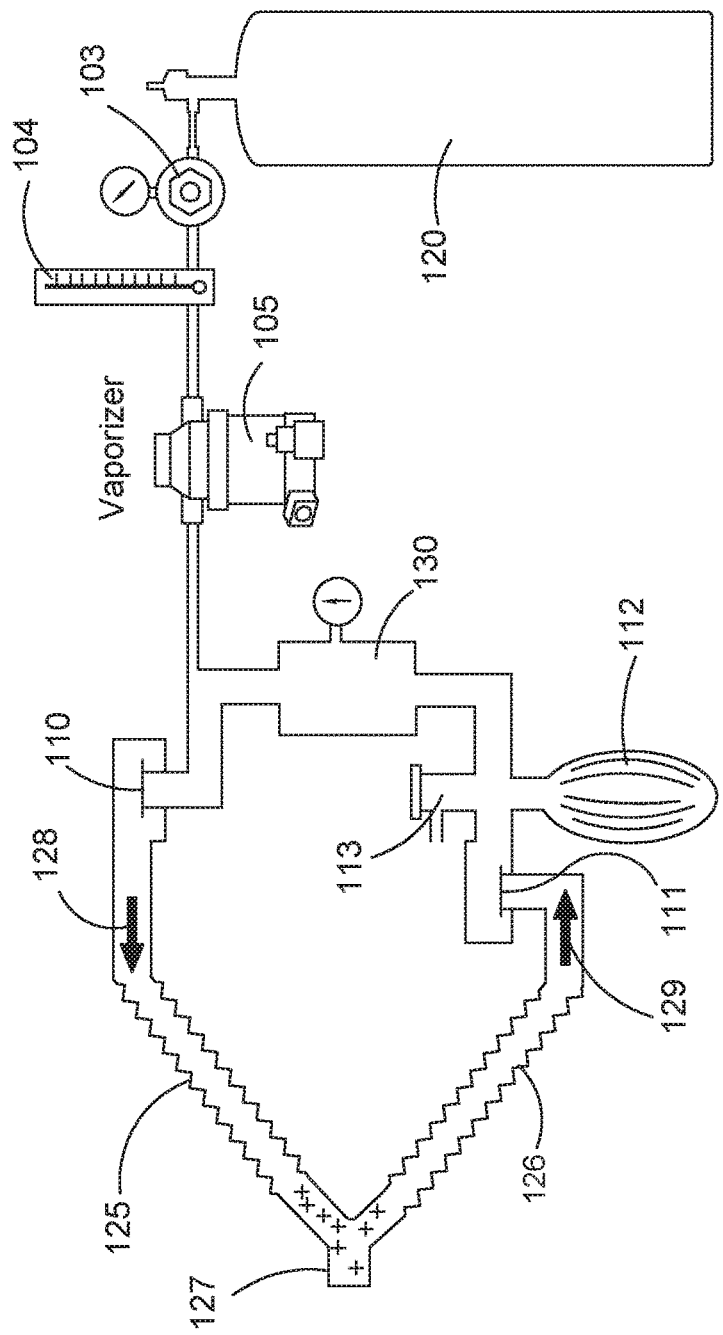
FIG. 17 is a diagram of a prior art Re-Breather circuit.

Referring to FIG. 17, a prior art Re-Breather circuit for delivering anaesthesia to a patient is illustrated. This circuit allows oxygen/air to be Re-Breathed after it has been scrubbed of carbon dioxide. The circuit includes a means of providing oxygen, in this case, a gas cylinder 120 containing oxygen. A regulator 103 is provided to regulate the pressure of the oxygen supply and a flow meter 104 provides an indication of the gas flow. A vaporiser 105 is provided for the introduction of anaesthetic (and perhaps other additional gases) to the gas flow. Anaesthesia lines 125 and 126 connect to a "Y" piece 127 which may connect to a mask (not shown) as an interface with the patient. Fresh Gas flow comes down inspiration line 125 from the vaporiser 105 and from the rest of the circuit. Direction of gas flow is shown by arrow 128.

Exhaled (exhaust) gas flow travels up the other arm, expiration arm 126 in the direction of arrow 129. Scrubber 130, which in this embodiment may be canister containing soda lime or alternative carbon dioxide scrubber, removes carbon dioxide from the exhaled gas. The scrubbed gas is returned to the inspiration line 125 at the other side of the scrubber 130.

The anaesthetic circuit also comprises an inhalation valve 110 and an exhalation valve 111 which are one way valves arranged to maintain flow of gas in the direction of arrows 128 and 129.

A breathing bag 112 is provided for damping pressure fluctuations due to inhalation and exhalation. A "pop off" valve 113 is provided to release a mass of gas equal to the mass of Fresh Gas delivered to the Re-Breather circuit minus the $CO_2$ absorbed by the scrubber 130.

As discussed above, Re-Breather circuits have a number of disadvantages, in particular for use with smaller patients.

One of the problems is poor dynamic response due to the large volumes that may be present in such circuits.

Figure 1:
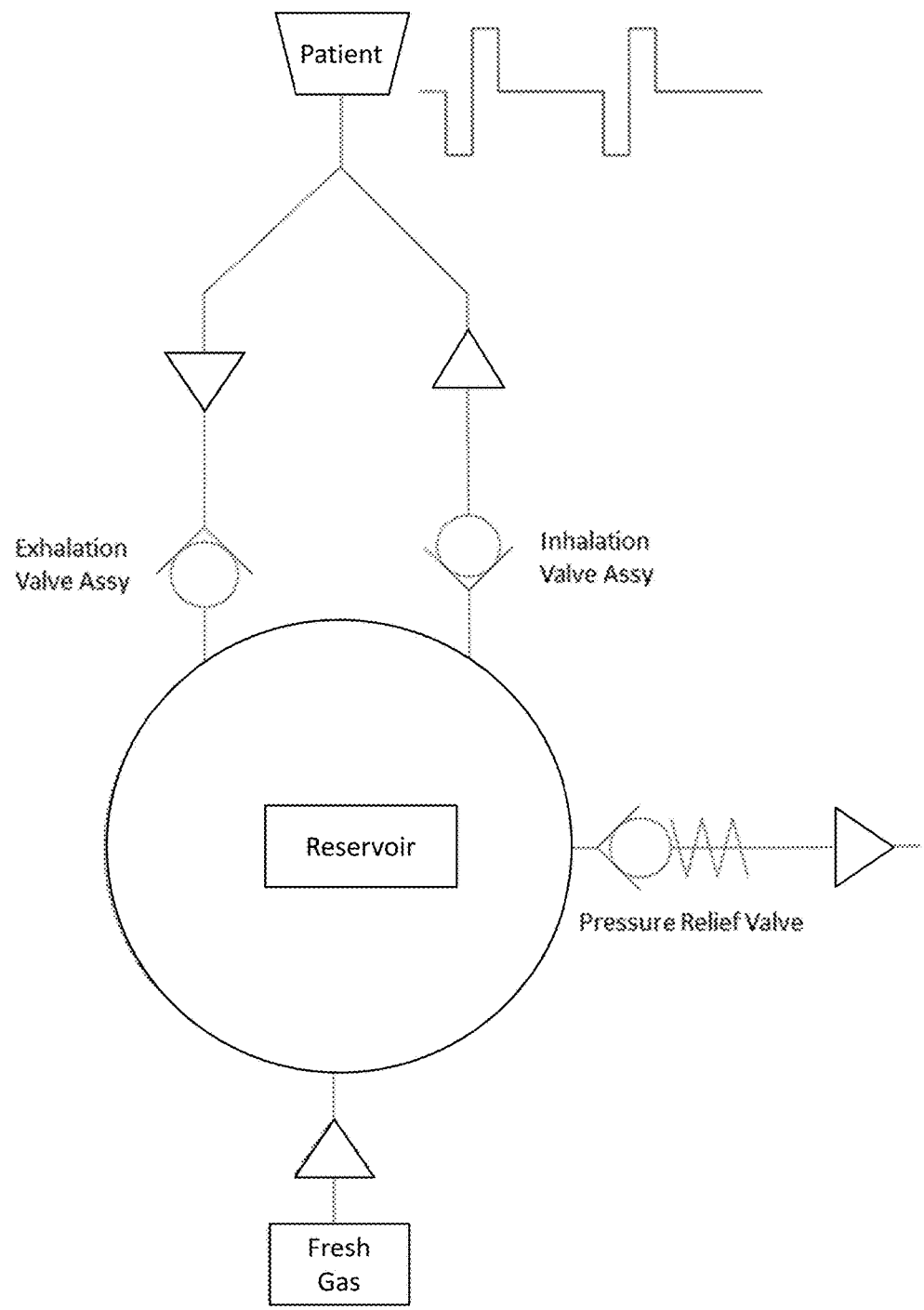
FIG. 1 is a simple model of a prior art Re-Breather circuit.

The interaction of circuit volume, patient tidal volume and dynamic response are best understood by considering the operation of the Re-Breather circuit. FIG. 1 shows a simple model of a conventional Re-Breather circuit. The volumes created by the soda lime canister, the breathing bag, the internal passages and the valve manifold, in effect, form a large reservoir from which there are various gas inflows and outflows during any one cycle.

During steady state operation Fresh Gas (a mixture of carrier gas, usually $O_2$ and anaesthetic) is delivered to this reservoir by the vaporiser. During inhalation the patient draws a volume from this reservoir equal to the patient's tidal volume (Vt). This tidal volume contains a mixture of $O_2$ and anaesthetic gas at the reservoir concentration. During exhalation the patient returns a mixture of $O_2$, $CO_2$ and anaesthetic at reduced concentration to the reservoir. The $CO_2$ in this exhaled gas is absorbed by the Soda Lime. During this cycle a volume of gas equal to the volume of the Fresh Gas delivered minus the volume of $CO_2$ absorbed by the Soda Lime and the volume of anaesthetic absorbed by the patient is expelled from the reservoir through the pressure relief valve. This expelled gas carries with it anaesthetic at the reservoir concentration.

The absorption coefficient (β) describes the proportion of the anaesthetic delivered to the patient that is absorbed by the patient. If the concentration of gas being delivered to the patient is [R] then the concentration of anaesthetic returned to the reservoir during exhalation will be $[R] \times (1-\beta)$.

In the event the patient starts to wake up, the anaesthetist must deliver a rapid increase in the anaesthetic concentration to the patient. As the patient is drawing $O_2$ and anaesthetic from the reservoir, it is first necessary to increase the concentration of the anaesthetic in this reservoir. The reservoir's concentration is changed by increasing either the concentration or the flow rate of the Fresh Gas being delivered to the reservoir by the vaporiser or both. Over time this increases the concentration of the anaesthetic gas mixture in the reservoir and consequently the anaesthetic concentration drawn in by the patient during inhalation.

The increased Fresh Gas flow into the reservoir is accompanied by an increase in gas discharge through the pressure relief valve to the atmosphere. If the volume of $CO_2$ generated by the patient expressed as a proportion of the volume of Fresh Gas delivered to the Re-Breather circuit is γ, then the volume of gas discharged through the pressure relief valve will be proportional to (1−γ) FGF. This discharge carries with it anaesthetic at the reservoir's anaesthetic concentration, which consequently reduces the amount of anaesthetic in the Re-Breather circuit.

Consequently:

Anaesthetic mass being delivered to reservoir is:

$\alpha FGF \times [FGF]$

Anaesthetic mass leaving the reservoir via pressure relief valve is:

$\alpha (1-\gamma) \times FGF \times [R]$

Anaesthetic mass taken from reservoir during inhalation $\alpha \dot{V}t \times [R]$ Anaesthetic mass returned to reservoir during exhalation $\alpha \dot{V}t \times [1-\beta]$ Change of anaesthetic mass in the reservoir is:

$\alpha V_R \times d[R]$

Using conservation of anaesthetic mass:

$$V_R \times = d[R] = [FGF]) - ((1-\gamma) \times FGF \times [R]) - (\dot{V}t \times [R]) + (\dot{V}t \times (1-\beta) \times [R])$$

where:
FGF Flow rate of Fresh Gas into the reservoir
[FGF] Concentration of anaesthetic in the Fresh Gas flow
[R] Concentration of anaesthetic in the reservoir
Vt Patient's tidal volume flow rate (=patient's tidal volume× patient's respiratory rate)
$V_R$ Reservoir volume
β Proportion of anaesthetic delivered during inhalation absorbed by the patient.
γ The volume of $CO_2$ as a proportion of the volume of Fresh Gas delivered to the Re-Breather circuit.
d[R] Rate of change of anaesthetic concentration in reservoir.

Figure 13:
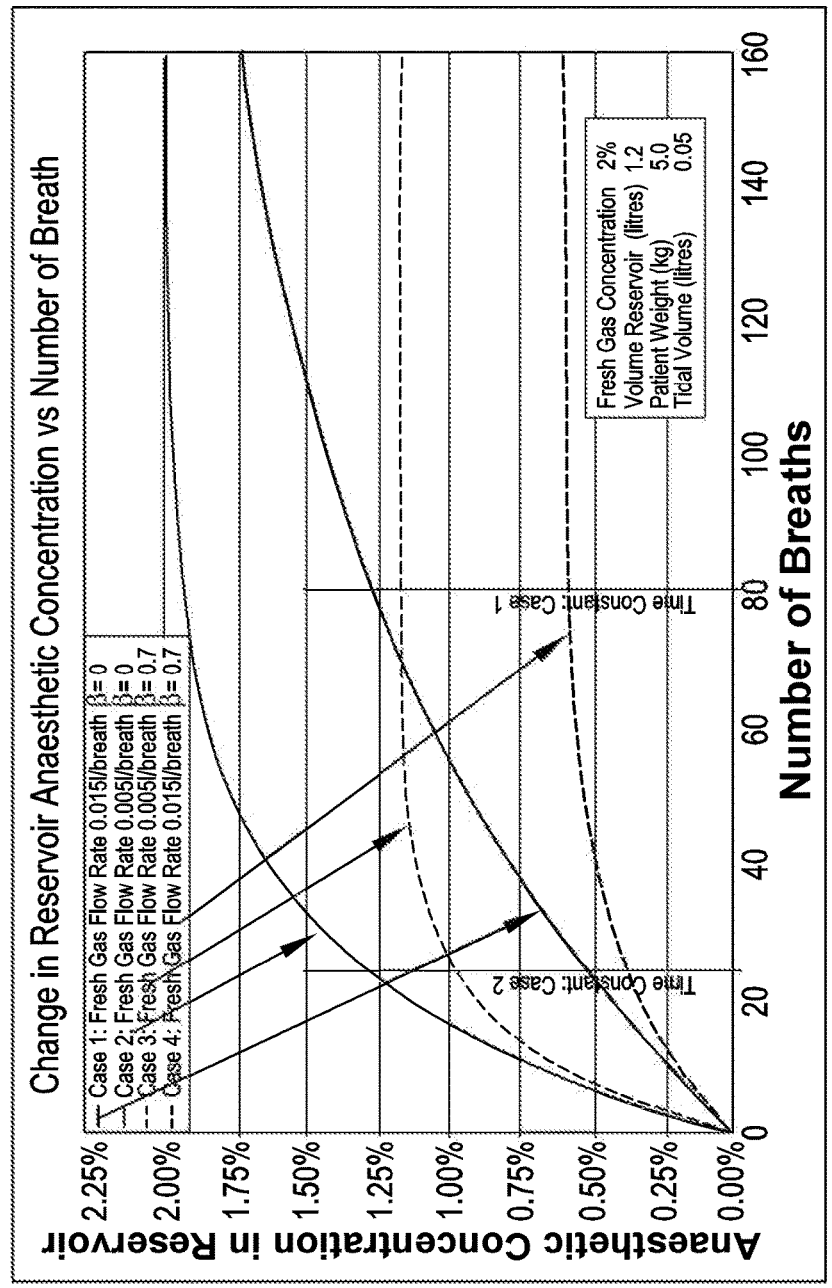
FIG. 13 shows response of a prior art Re-Breather circuit to a step change in the anaesthetic concentration of the Fresh Gas.

This equation can be rearranged to calculate the change in reservoir concentration for every breath the patient takes. FIG. 13 shows the results for a 5 kg dog (tidal volume 50 ml) attached to a typical Re-Breather circuit with a reservoir volume of 1.2 liters. There is initially no anaesthetic in the Re-Breather circuit and the Fresh Gas has an anaesthetic concentration of 2%. FIG. 13 examines the effect of Fresh Gas flow rate (30% and 100% of the patient's tidal volume flow rate) and the effect of anaesthetic absorption by the patient (i.e. β=0 and β=0.7).

Figure 14:
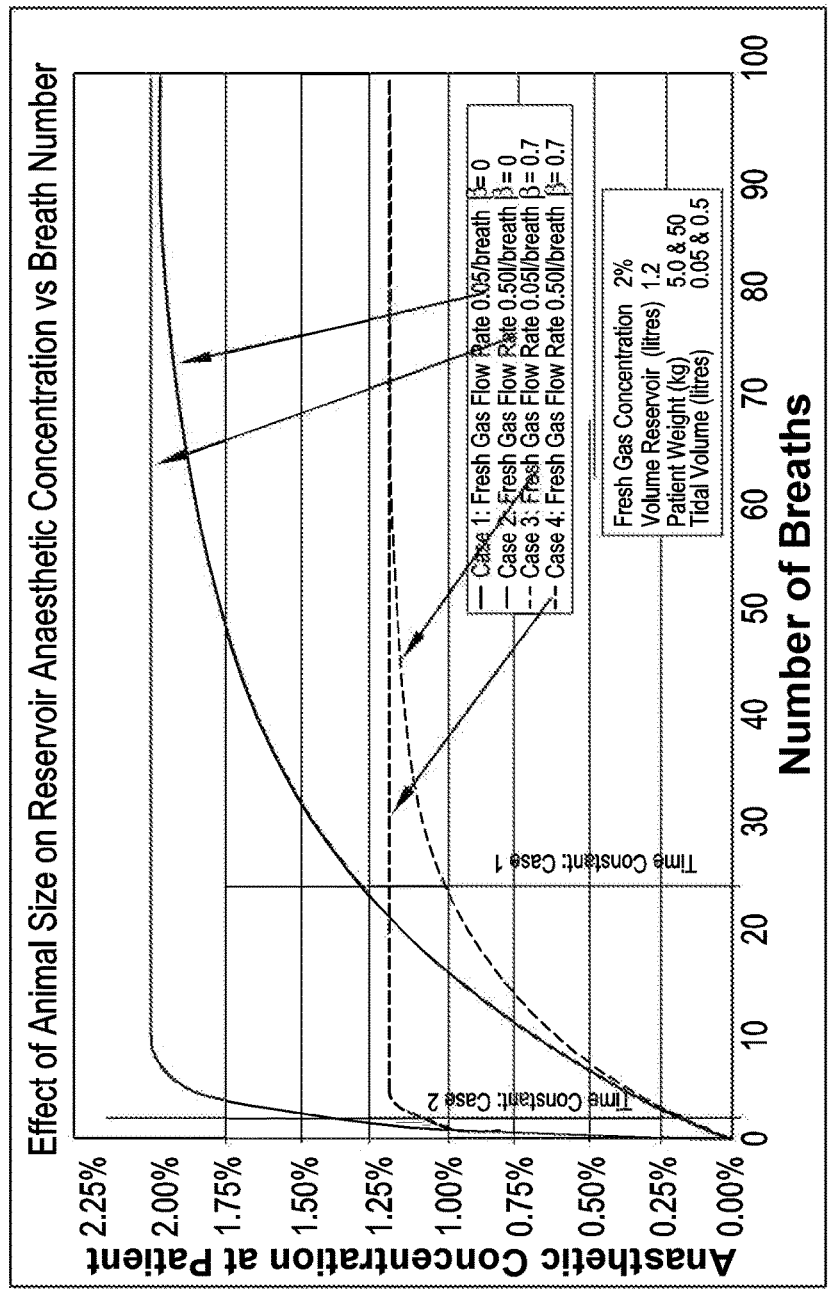
FIG. 14 shows how animal weight affects the response of a prior art Re-Breather circuit to a step change in the anaesthetic concentration of the Fresh Gas.

FIG. 14 illustrates how animal size affects the number of breaths required for the reservoir concentration to reach equilibrium after there is a step change in the concentration of the Fresh Gas. The Figure compares the number of breaths that a 5 kg animal and a 50 kg animal must take before the reservoir concentration reaches equilibrium assuming that the Fresh Gas flow rate is adjusted such that it equals the tidal volume flow rate of the patient. Two cases are examined; the case where there is no anaesthetic uptake by the patient (i.e. β=0) and the case where the patient absorbs 70% of the delivered anaesthetic (i.e. β=0.7). In both cases (β=0 and β=0.7) the 5 kg dog required 10 times the number of breaths taken by the 50 kg dog for the anaesthetic concentration of the reservoir to reach equilibrium.

There are several points of interest.

Firstly, at typical steady state Fresh Gas flow rates (30% of tidal volume flow rate) it takes an extraordinary long time for the reservoir anaesthetic concentration to approach that of the Fresh Gas. Even with no anaesthetic uptake by the patient it requires 200 breaths (approximately 20 minutes) for the reservoir concentration to reach 86% that of the Fresh Gas concentration (Case 1, FIG. 13).

The time constant for the circuit is defined as the time taken for the reservoir concentration to reach 63.2% that of the Fresh Gas concentration. It can be calculated by:

$$Tc = V_R / FGF.$$

In this particular example the Fresh Gas flow rate was 15 ml/minute or 1.5 ml per breath (assuming a respiratory rate of 10 breathes/minute) and the reservoir volume was 1.2 liters; Tc=120 ml/1.5 ml=80 breaths.

Secondly, in the case of the 5 kg animal even when the Fresh Gas flow rate is increased to that of the tidal volume flow rate, it still takes more than 100 breaths for the reservoir anaesthetic concentration to approach that of the Fresh Gas (Case 2, FIG. 13).

Thirdly, with the Fresh Gas flow rate equal to the tidal volume flow rate and the patient absorbing 70% of the anaesthetic gas delivered to it, the anaesthetic concentration of the reservoir gas reaches equilibrium at only 59% of the Fresh Gas concentration and even this takes some 60 breaths to achieve (Case 3, FIG. 13).

Finally, the number of breaths required for the reservoir anaesthetic concentration to reach equilibrium is inversely proportional to the patient's tidal volume or weight, irrespective of whether the patient absorbs anaesthetic (Cases 3 and 4, FIG. 14) or the patients does not absorb anaesthetic (Cases 1 and 2, FIG. 14).

Figure 22:
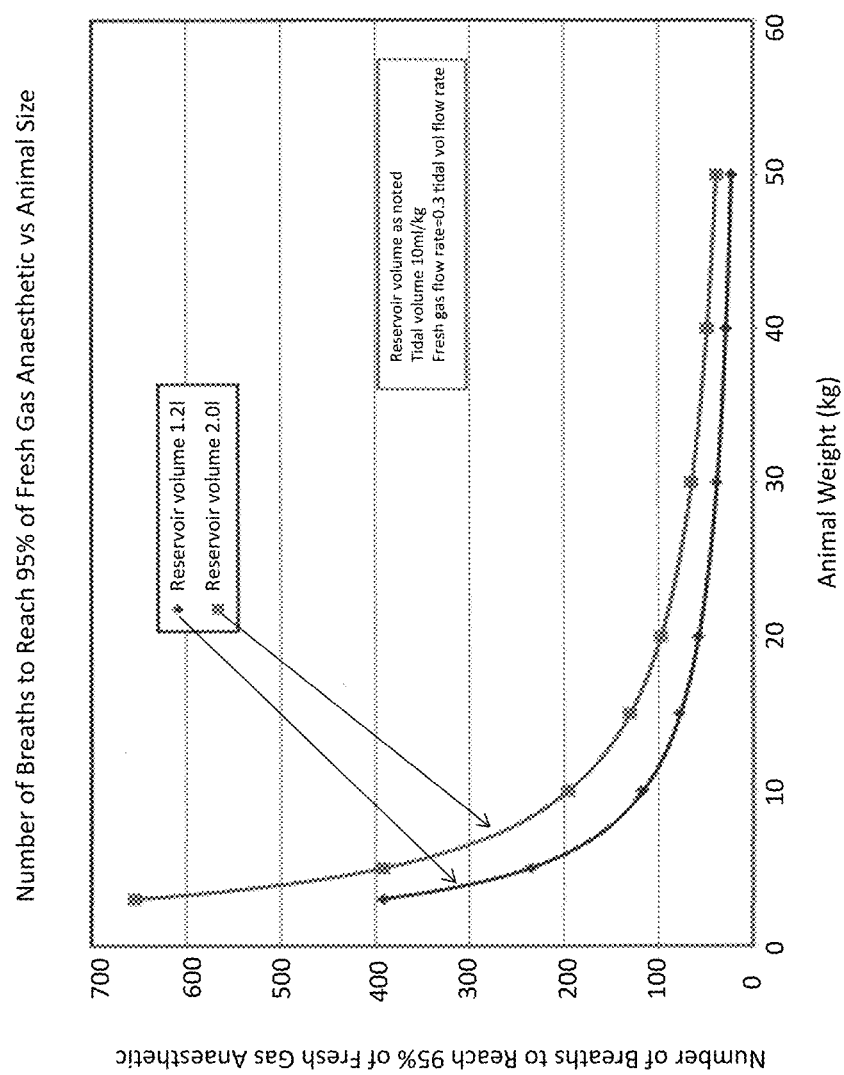
FIG. 22 shows how animal size and reservoir volume affect the dynamic response of a prior art Re-Breather circuit to a step change in the anaesthetic concentration of the Fresh Gas.

Thus, in conventional Re-Breather circuits, the rate of change of anaesthetic concentration (i.e. the dynamic response) is inversely proportional to the reservoir volume (i.e. the larger the reservoir volume the slower the response, i.e. the response time increases) and directly proportional to the patient's size or tidal volume (i.e. the larger the animal the faster the response, i.e. response time decreases). These relationships are shown in FIG. 22. It is clear from an examination of this Figure, why the delivery of anaesthetic to animals weighing less than 20 kgs is such a difficult task.

Consequently, the rate of change of anaesthetic concentration at the patient is inversely proportional to the ratio of the reservoir volume to the patient's tidal volume.

For optimal dynamic response the Re-Breather circuit should, therefore, be designed and manufactured for specific patient sizes. Commercial reality, however, dictates that Re-Breather circuits are designed so that one model operates effectively with all patient sizes. Conventional Re-Breather circuits used in veterinary medicine, for example, are typically used on patients weighing between 70 kg and 10 kg. The cross sectional areas of the flow passages must be designed such that there is little resistance to flow when even the largest animals are attached. As these cross sectional flow areas are a major determinant of the volume of the Re-Breather circuit, the Re-Breather circuit volume is dictated by the heaviest patients that the circuit must accommodate.

Re-Breather circuits typically have considerable volume; in the order of 1.2 liters plus. In the case of a 70 kg dog, the reservoir volume is 1.7 times the dog's tidal volume. In the case of a 5 kg dog the reservoir volume is 24 times the dog's tidal volume and the dynamic response will be reduced by a factor of approximately 14. While the dynamic response of this Re-Breather circuit may be suitable for a 70 kg dog, it will not be suitable for a 5 kg dog.

In the event the patient starts to wake up during surgery, it is clearly of the utmost importance to be able to deliver a rapid increase in the anaesthetic concentration to the patient. The volume of conventional Re-Breather circuits is a fundamental obstacle to satisfying this requirement when small patients (e.g. patients smaller than 10 to 15 kg) are attached to these circuits.

Figure 16:
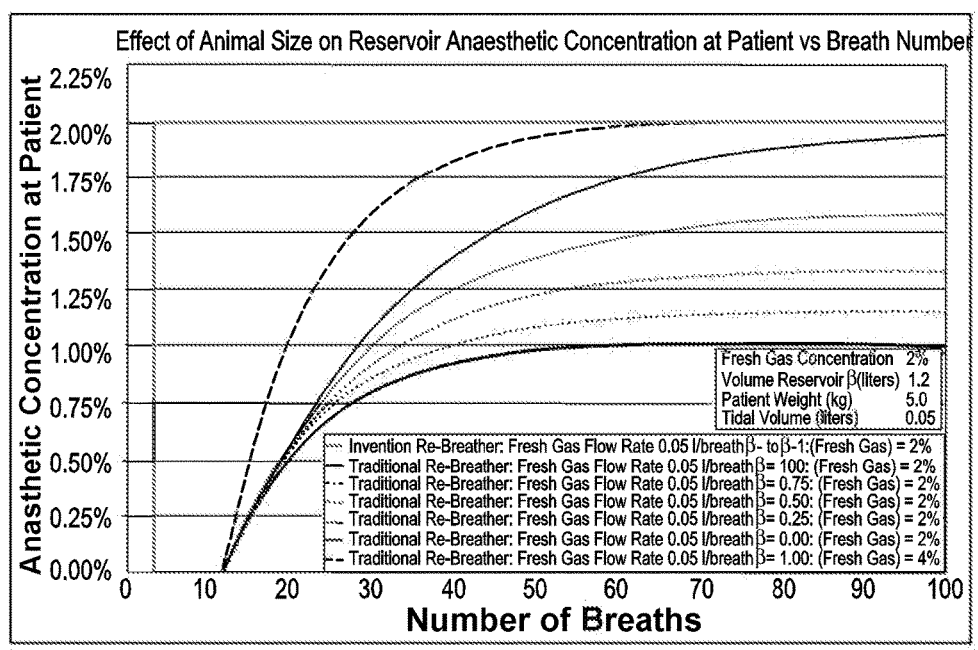
FIG. 16 is a plot comparing the response of an apparatus in accordance with an embodiment of the present invention, to a step change in anaesthetic concentration of the Fresh Gas with that of a prior art Re-Breather circuit when the Fresh Gas flow rate equals the patients tidal volume flow rate.

A compounding problem occurs in the inhalation hose which also has significant volume—a fact not considered in the modelling considered above. Typical inhalation hoses have a diameter 22 mm and a length of 1.5 m giving them a volume of 570 ml. If we assume that there is no mixing in the hose then it will take a considerable time for the higher concentration anaesthetic entering the inhalation hose to find its way to the patient. In the case of a 5 kg animal with a tidal volume of 50 ml it will take 11 breathes to travel to the patient. The rise in concentration of the reservoir shown in FIGS. 13 and 14 will be therefore be delayed a further 11 breaths before it reaches the patient. This delay is shown in FIG. 16.

This particular problem becomes greater the smaller the animal (i.e. the smaller the tidal volume). For instance if the inhalation hose discussed above was used to deliver anaesthetic to an animal with a tidal volume of 25 ml rather than 50 ml the animal would require 22 breaths before it first saw any increase in the concentration delivered from the reservoir.

Thus like the reservoir, the inhalation hose reduces the dynamic response, delaying the delivery of increased anaesthetic concentrations by a time that is inversely proportional to the patient's tidal volume or size and directly proportional to the volume of the inhalation hose.

The model discussed above is a simplification of actual Re-Breather circuits. However, it has the merit of providing an easy demonstration of the basic limitation of all conventional Re-Breather circuits; that is it takes a very long time between the anaesthetist acting to increase the anaesthetic concentration and the delivery of the increased concentration to the patient.

Real world systems differ in three important respects. Firstly, the model assumes complete mixing of the Fresh Gas with the contents of the reservoir. Real world Re-Breather circuits are not a single large reservoir but a series of interconnected passages and volumes which do not allow the complete mixing of anaesthetic gas to a uniform concentration. How accurately this model predicts the actual mixing in these circuits depends on the details of each individual circuit.

Secondly, in many Re-Breather circuits the Fresh Gas is delivered adjacent the inhalation valve, which together with the plumbing and the system of one way valves makes it possible for a portion of the Fresh Gas to be delivered directly to the inhalation hose rather than exclusively to the reservoir as the simple model assumed.

Finally, in many Re-Breather circuits the pressure relief valve is located adjacent the exhalation valve where a portion of the gas discharged can be drawn from the exhalation hose rather than exclusively from the reservoir as the simple model assumed.

Figure 2:
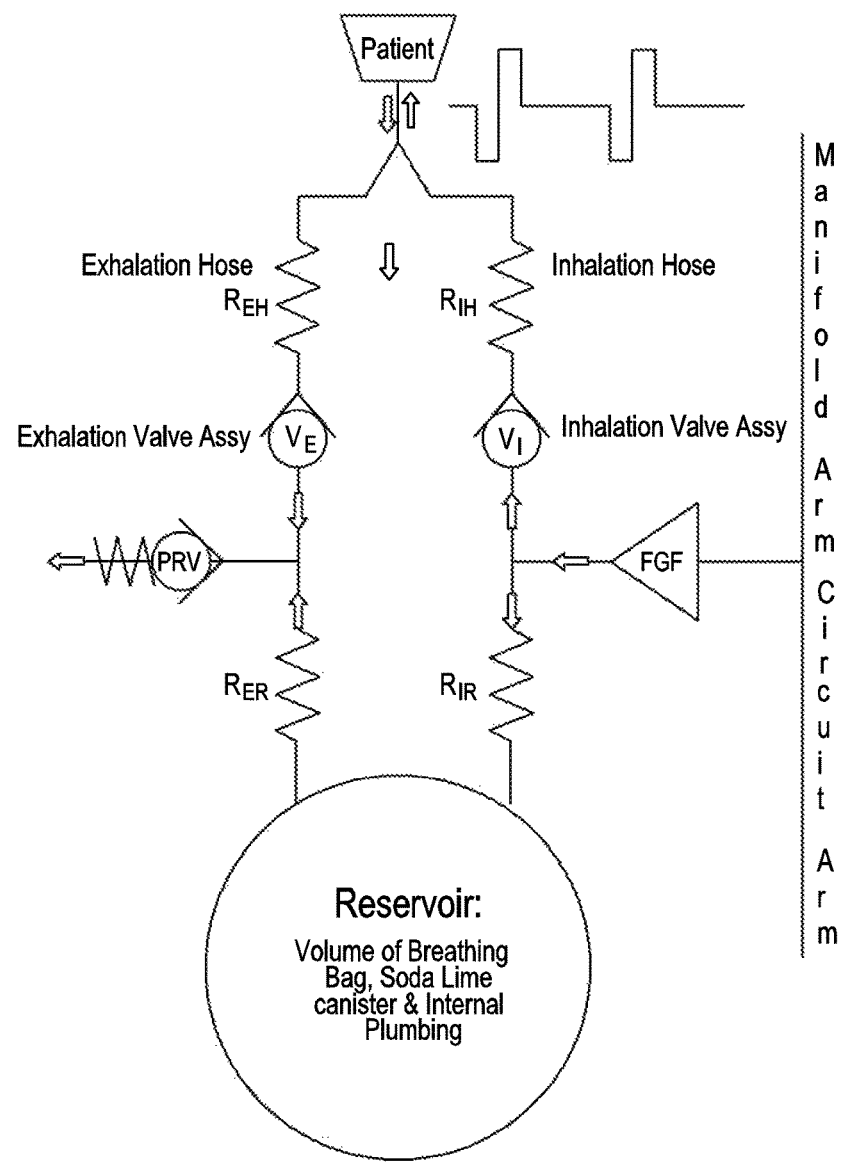
FIG. 2 is a more complex model of a prior art Re-Breather circuit.

A flow model that better takes these real world limitations into account is shown in FIG. 2. For the purpose of this analysis we can consider the Re-Breather circuit to comprise two arms; the circuit arm and the manifold arm. The circuit arm comprises a volume (the reservoir volume) and two flow resistances (the flow resistance of the passages leading to and from the reservoir volume). The reservoir volume comprises the volume of the soda lime container, the breathing bag and the internal passages in the circuit arm.

The manifold arm comprises two one way valves (the inhalation valve and the exhalation valve) and two flow resistances. The first flow resistance comprises the flow resistance of the inhalation valve, the inhalation hose and the Y piece. The second flow resistance comprises the flow resistance of the Y piece, the exhalation hose and the exhalation valve.

It is clear from a consideration of this model that, unlike the previous simple model, Fresh Gas delivered to the Re-Breather circuit can flow both through the circuit arm and the manifold arm and that gas expelled from the Re-Breather circuit through the pressure relief valve can flow from both the circuit arm and the manifold arm.

The proportion of Fresh Gas that flows through each of these two arms (and therefore the proportion of gas that will flow from these two arms to the pressure relief valve) will depend on the relative flow resistance of these paths and the type of excitation applied to the Re-Breather circuit by the patient.

Figure 15:
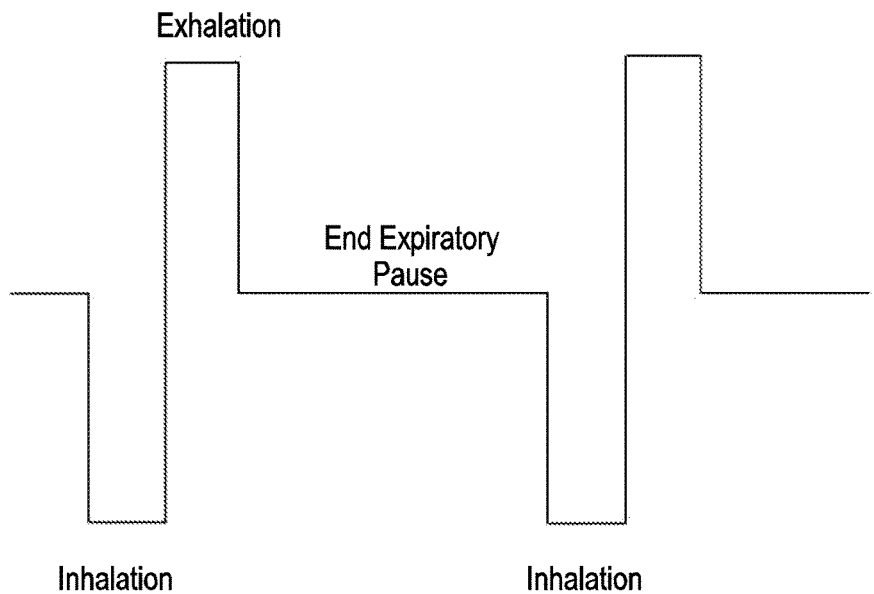
FIG. 15 is a diagram illustrating a typical breathing cycle of a patient.

The patient provides cyclic excitation of the circuit which has three distinct phases; Inhalation, Exhalation and End Expiratory Pause. These phases are shown in FIG. 15. The average cycle time for an animal is typically 6 seconds of which inhalation occupies approximately one second, exhalation one second and end expiratory pause four seconds.

The direction of Fresh Gas flow in the Re-Breather circuit depends primarily on which phase of the cyclic excitation the Re-Breather circuit is experiencing.

During inhalation all the gas flow in the Re-Breather circuit is towards the patient and all Fresh Gas delivered during this phase will flow directly into the inhalation hose. There will be no Fresh Gas flow to the reservoir as the previous simple model assumed.

During exhalation, pressure in the manifold arm will prevent the inhalation valve opening and all Fresh Gas flow will be into the circuit arm and the reservoir.

During the end expiratory pause phase there is no external excitation of the circuit and the ratio of the Fresh Gas that passes through the circuit arm and manifold arm will be inversely proportional to the flow resistance of these arms. Using the terminology of FIG. 2:

$$\frac{Qcircuit}{Qmanifold} = \frac{Rmanifold}{Rcircuit} = \frac{(RIH + REH + RVi + RVe)}{(RIR + RER)}$$

where:
Qcircuit Flow rate through the circuit arm
Qmanifold Flow rate through the manifold arm
RIH Flow resistance of the inhalation hose and Y piece
REH Flow resistance of the exhalation hose and Y piece
RVi Flow resistance of inhalation valve
RVe Flow resistance of exhalation valve
RIR Flow resistance of internal passages downstream of reservoir
RER Flow resistance of internal passages upstream of reservoir
(RIH+REH+RVi+RVe) Flow resistance of the manifold arm
(RIR+RER) Flow resistance of the circuit arm The terms "upstream" and "downstream" are used in relation to the direction of gas flow induced by the patient in the circuit. This will be towards the patient in the inhalation arm and away from the patient in the exhalation arm, being anti-clockwise through the circuit (see FIGS. 17 and 19). Note that the Fresh Gas can, at times, flow in the opposite direction.

The resistance of the manifold arm is high due to the presence of the inhalational and exhalation valves and the long length of hoses connecting the patient to the Re-Breather circuit. Typically, in a well-designed Re-Breather circuit, the resistance of the manifold arm is several multiples that of the circuit arm and could be, depending on the design of the valves, as high as 10 times that of the circuit arm.

Assuming the flow resistance of the manifold arm is 10 times that of the circuit arm the proportion of Fresh Gas flowing into the circuit arm is:

| | |
|---|---|
| During the inhalation phase | 0% of 1/6 = 0.0 |
| During the exhalation phase | 100% of 1/6 = 0.17 |
| During the end expiratory pause | 90% of 4/6 = 0.6 |

Over the cycle the proportion of Fresh Gas flowing to the circuit arm and the reservoir is 77%; a result which validates the use of the simple model.

The problem of the long delay between an increase in the anaesthetic concentration of the Fresh Gas and this increased concentration first being seen by the patient would be addressed if all the Fresh Gas was delivered into the manifold arm and none to the circuit arm. In this situation the only delay would be the length of time required for the Fresh Gas to transit to the patient through the inhalation hose. The delay caused by reservoir mixing would be eliminated.

For this to occur the Re-Breather circuit would need to be designed such that the flow resistance of the circuit arm was several (ten or more) multiples greater than that of the manifold arm. While this could be easily achieved by deliberately designing flow passages with small cross sectional area in the circuit arm, it would introduce other problems (excessive flow resistance) during inhalation and exhalation as the following discussion illustrates.

The average inhalation flow rate over the complete cycle is the animal's tidal volume multiplied by the animal's respiratory rate; typically 10 times tidal volume per minute. As inhalation and exhalation each occupy only one sixth of the cycle the peak inhalation flow rate and exhalation flow rate is typically six times the average inhalation flow rate; i.e. 60 times the tidal volume per minute. The steady state Fresh Gas flow rate is typically in the order of 0.3 times the tidal volume flow rate. Consequently the peak flow rates during inhalation and exhalation are in the order of 200 times those of the Fresh Gas flow rate.

As it is the patient's lungs that provides the driving force for these peak flow rates through the Re-Breather circuit, it is essential that the peak flow rates can be accommodated without the patient having to generate excessive pressure in its lungs; i.e. the flow channels in the Re-Breather circuit must be designed to accommodate these peak flow rates without large pressure drops and must consequently have low resistance to flow. Typically the peak flow rate must generate pressure drops less than 5 cm $H_2O$ and preferably only 2 cm $H_2O$.

This consideration prevents the circuit arm being redesigned to increase its flow resistance. As previously discussed, the circuit arm typically has a flow resistance as low as one tenth that of the manifold arm. In order to effect an arrangement where the Fresh Gas flow was predominantly directed down the manifold arm, the circuit arm flow resistance would have to be increased in the order of 100 fold (i.e. in order to transform its flow resistance from $1/10$ of the manifold arm's flow resistance to 10 times that of the manifold arm). Such a system would have an overall flow resistance more than 10 times greater than the current systems which are already close to the practical limit for larger animals attached to the Re-Breather circuit.

For practical Re-Breather circuits it is therefore inevitable that the majority of the Fresh Gas flow will be directed down the circuit arm where it will be mixed with the existing anaesthetic mixture and diluted before being drawn into the inhalation hose and delivered to the patient.

Figure 19:
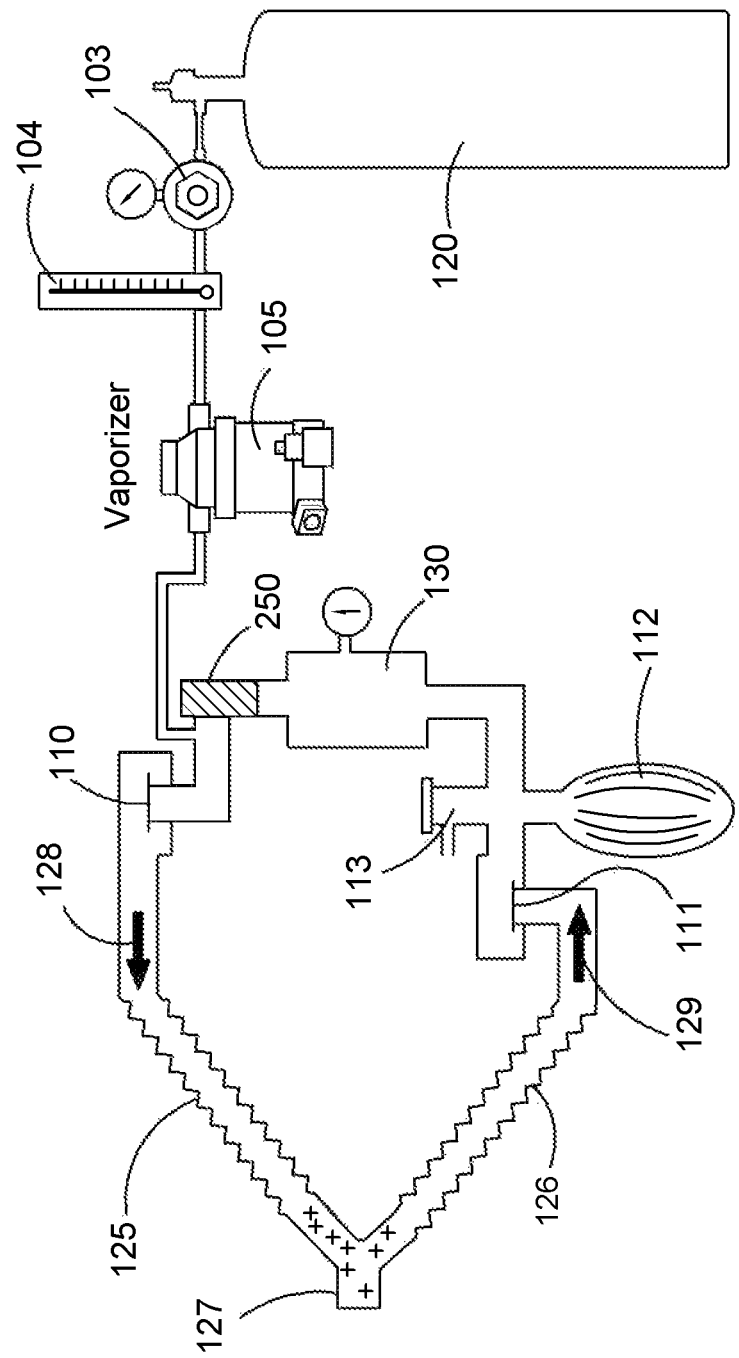
FIG. 19 is a schematic diagram of a Re-Breather circuit incorporating an anaesthetic apparatus in accordance with an embodiment of the present invention.

FIG. 19 is a diagram of a Re-Breather anaesthetic circuit incorporating an anaesthetic apparatus in accordance with an embodiment of the present invention.

In this figure, the same reference numerals have been used as in FIG. 17 for the same components, and no further description of these components will be given here. In addition to these prior art components, the Re-Breather circuit of FIG. 19 incorporates an anaesthetic apparatus 250, comprising a conservation arrangement which is arranged to slow mixing of the Fresh Gas from the vaporiser 105 with the anaesthetic gas in the rest of the circuit. The conservation arrangement is arranged to store the Fresh Gas entering the anaesthetic circuit in a manner that minimises the dilution of the Fresh Gas by the gas already resident in the anaesthetic circuit. In use, the conservation arrangement reduces the flow of Fresh Gas away from the inhalation valve 110 and Fresh Gas inlet area 257 into the rest of the anaesthetic circuit, so conserving Fresh Gas proximate the inhalation arm 128. So that when the patient breathes in, then Fresh Gas which is undiluted or predominantly undiluted is available to be drawn into the inhalation arm 128. This therefore improves the dynamic response of the circuit.

The conservation arrangement may comprise any apparatus that operates to slow the mixing of Fresh Gas entering the circuit with gas already present in the circuit. In the following, detailed descriptions are given of anaesthetic apparatus comprising conservation arrangements which comprise accumulators having different configurations designed to store Fresh Gas and reduce mixing. The invention is not limited to these accumulator configurations, however, and other conservation arrangements may be implemented.

Figure 3:
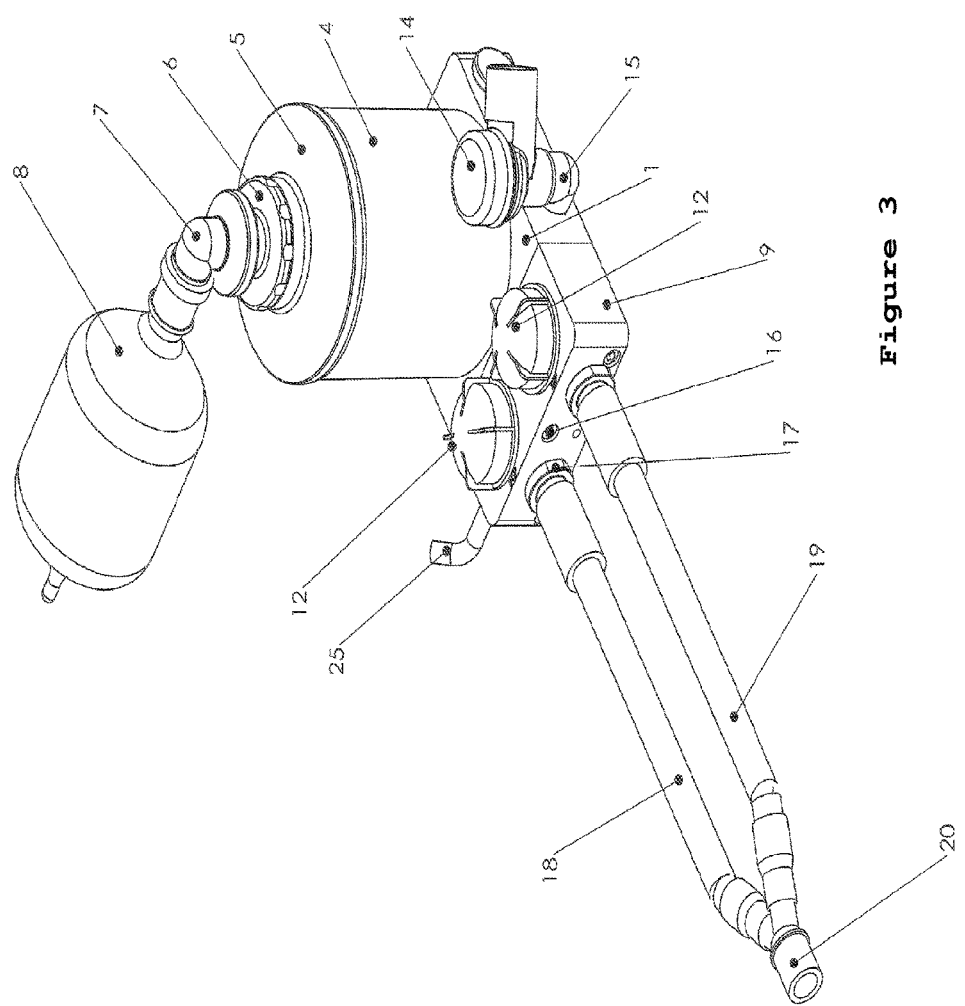
FIG. 3 is a perspective view from above and one side of an anaesthetic apparatus in accordance an embodiment of the present invention.
Figure 4:
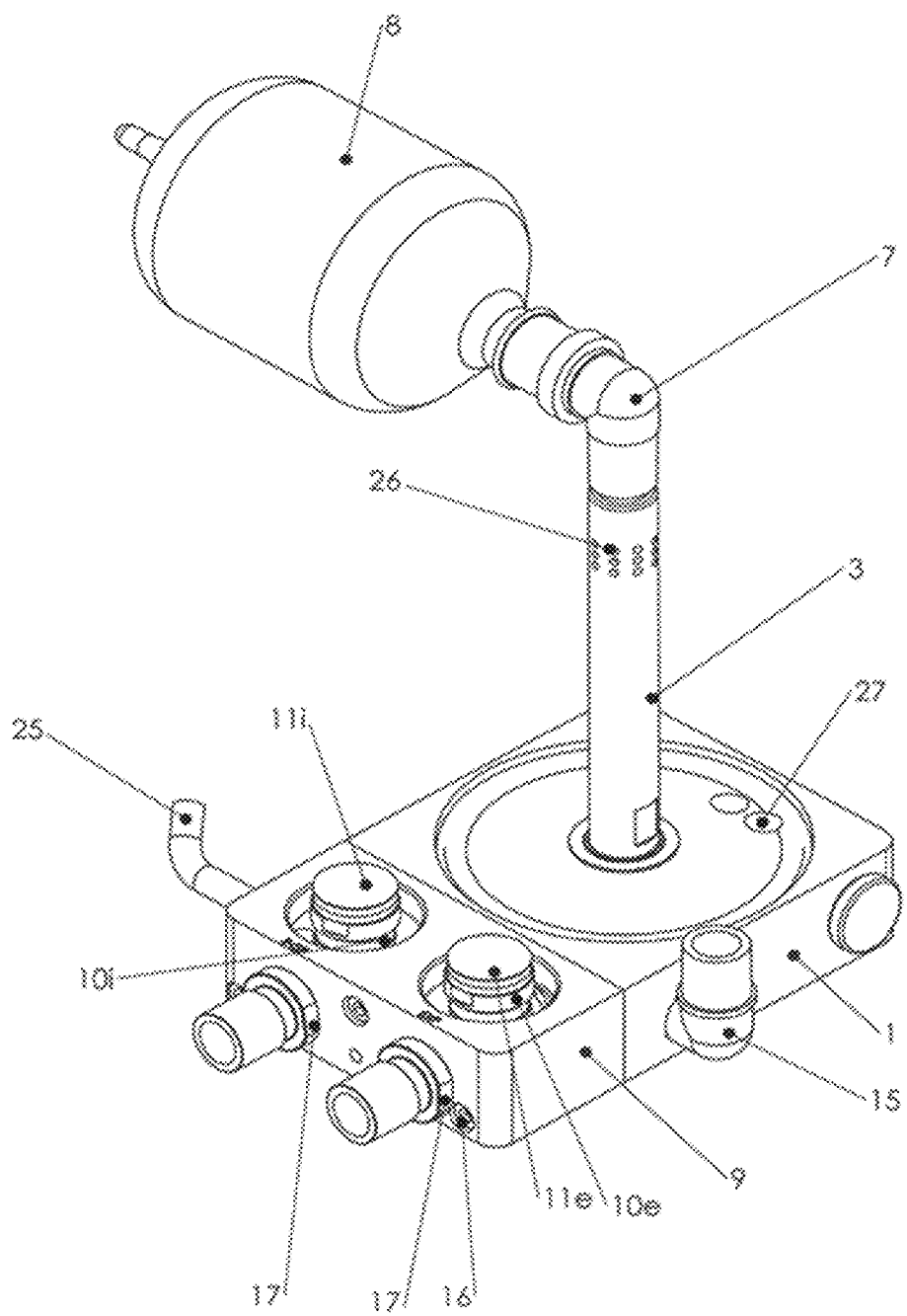
FIG. 4 is a view of a part of the apparatus of FIG. 3, with some components removed to show other components of the apparatus.
Figure 5:
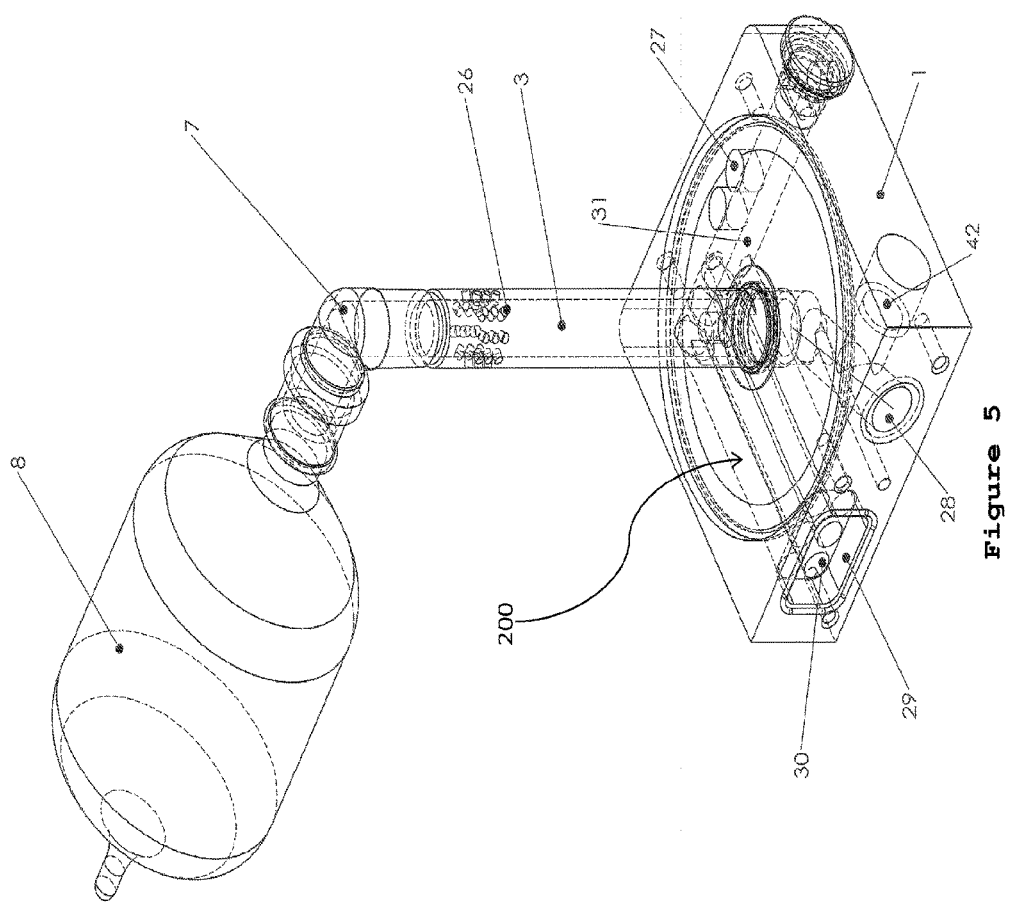
FIG. 5 is a view of part of the apparatus of FIG. 3, showing internal components in ghost outline.
Figure 7:
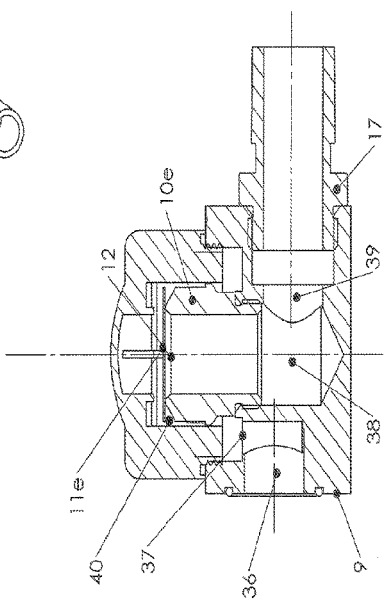
FIG. 7 is a cross-sectional view through an exhalation valve assembly of the apparatus of FIG. 3.
Figure 8:
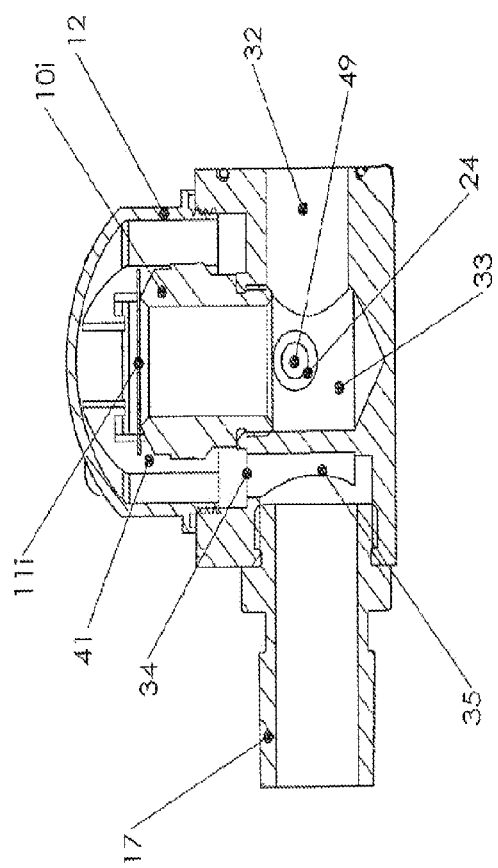
FIG. 8 is a cross-sectional view through an inhalation valve assembly of the apparatus in FIG. 3.
Figure 9:
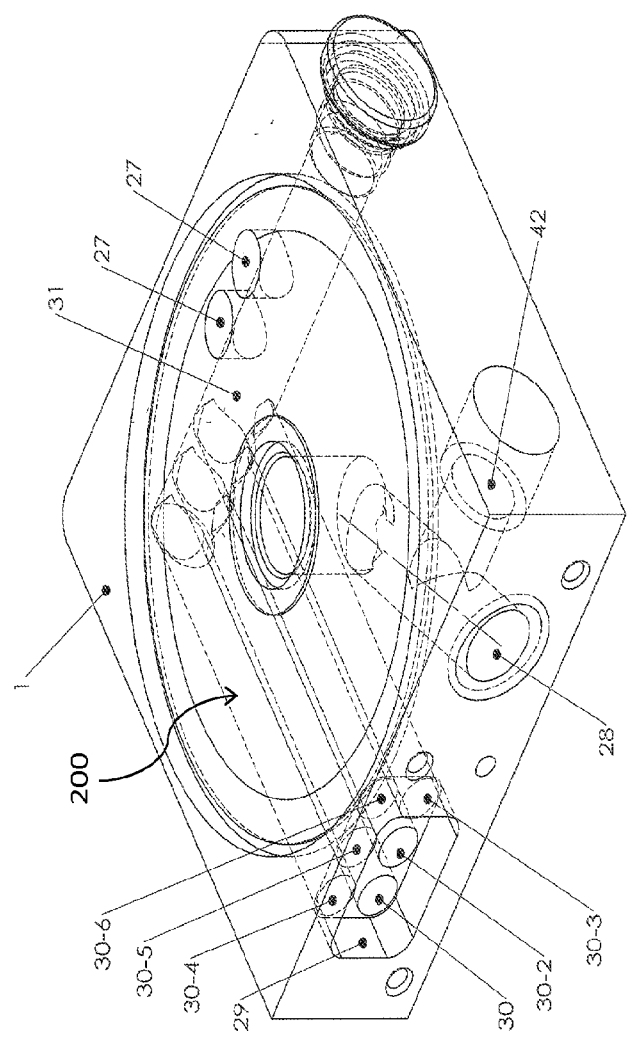
FIG. 9 is a further perspective view of a part of the apparatus of FIG. 3 with internal components shown in ghost outline.

A Re-Breather circuit comprising an apparatus in accordance with an embodiment of the present invention is illustrated in FIGS. 3 to 9. In an embodiment, an anaesthetic apparatus comprises a conservation arrangement which is generally designated by reference numeral 200 (FIGS. 5 and 9). The conservation arrangement is arranged to slow mixing of Fresh Gas entering the anaesthetic circuit (in this embodiment comprising the other components shown in FIGS. 3 to 9, but not limited to these components), with gas already contained in the anaesthetic circuit. In this embodiment, the conservation arrangement 200 comprises an accumulator 30 which is arranged to accumulate Fresh Gas entering the anaesthetic circuit, and, store it proximate an inspiration arm of the circuit.

Figure 6:
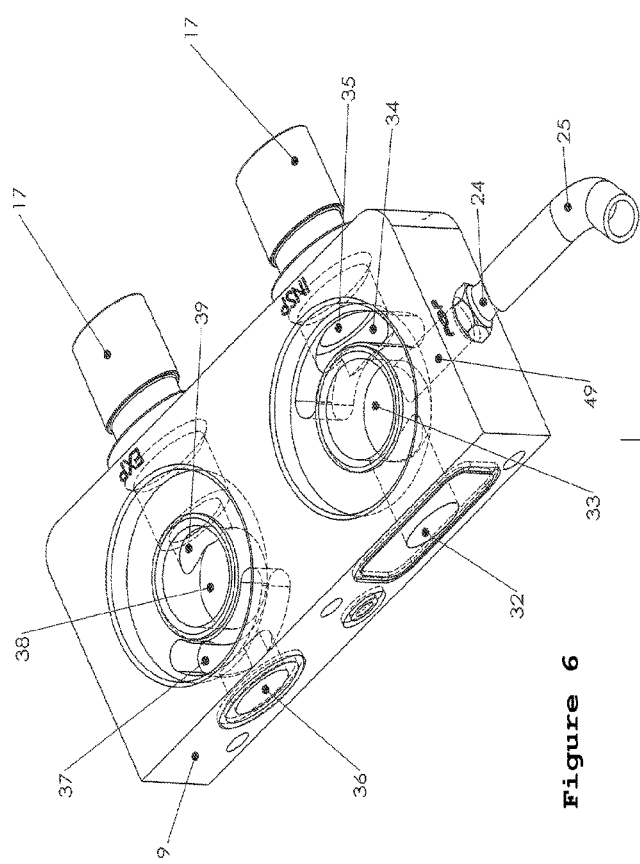
FIG. 6 is a view of a valve manifold of the apparatus of FIG. 3, showing internal components in ghost outline.

The Re-Breather Circuit shown in FIG. 3 comprises a housing, in this embodiment in the form of a baseplate 1, a container to hold the soda lime comprising a soda lime canister 4 and lid 5, a means of attaching the soda lime container to the baseplate comprising cap 6, a breathing bag 8, an elbow 7 for attaching the breathing bag to the cap 6, a valve manifold 9 attached to baseplate 1 via screws 16, connectors 17 for attaching the inhalation hose 18 and exhalation hose 19 to valve manifold 9, a Y piece 20 connecting the patient to the inhalation hose 18 and exhalation hose 19, valve covers 12, and a pressure relief valve 14 attached to baseplate 1 by elbow 15. Fresh Gas is supplied to the Re-Breather circuit from a vaporiser (not shown) by hose 25, fitting 24 (FIG. 6) and Fresh Gas port 49 (FIG. 6).

In FIG. 4 the soda lime canister 4, lid 5 and cap 6 have been removed to reveal the internal plumbing. Tube retainer 3 is secured to the baseplate 1 at one end. Cap (not shown) screws to the other end of tube retainer 3 thereby anchoring soda lime container 4 and lid 5 to the baseplate. Tube retainer 3 is hollow and provides a flow path between breathing bag 8 and exhalation hose 19 via internal passages in baseplate 1 and valve manifold 9. It also provides a flow path between breathing bag 8 and pressure relief valve 14 via internal passages in baseplate 1 and elbow 15.

The valve manifold 9 houses two one way valve assemblies. The inhalation valve assembly consists of a valve seat 10*i* and a disc valve 11*i* which seals against a knife edge on valve seat 11*i*. This one way valve assembly allows the flow of gas from the valve manifold to the inhalation hose 18 and prevents flow from the inhalation hose 18 back into valve manifold 9.

The exhalation valve assembly consists of valve disc 11*e* and valve seat 10*e*. It allows the flow of gas from the exhalation hose 19 into the valve manifold 9 but prevents any flow from the valve manifold 9 into the exhalation hose 19.

In FIG. 5 the valve manifold 9 has been removed to reveal the internal passages in baseplate 1. Internal passage in retaining tube 3 connects to the exhalation internal passage 28 which in turn connects with exhalation valve assembly comprising valve seat 10e and disc valve 11e. Internal passage 42 connects exhalation internal passage 28 to pressure relief valve 14 via elbow 15.

Retaining Tube 3 has tube exit holes 26 adjacent its upper end which allows exhaled gas to enter the soda lime canister 4. The exhaled gas passes through the soda lime (not shown) and exits through openings in the base of the soda lime canister into baseplate 1 through baseplate entry holes 27. These holes communicate with the inhalation valve assembly via baseplate internal inhalation passages 29 and 31 and by the internal passages in accumulator 30.

FIG. 6 shows the valve manifold assembly with the valve assemblies 10 and 11 and valve caps 12 removed to allow easy observation of the flow passages in the valve block 9. A section through the centre of the exhalation valve assembly is shown in FIG. 7 and through the centre of the inhalation valve assembly in FIG. 8.

With reference to FIG. 7, gas flow from the exhalation hose 19 enters the valve manifold 9 through fitting 17 into passage 39 which delivers gas to manifold exhalation entry chamber 38. Gas flows from this chamber through the internal passage in valve seat 10e where it lifts the disc valve 11e off its seat and allows gas to discharge into manifold exhalation exit chamber 40. From there it passes through passage 37 into passage 36 which connects to passage 28 in the baseplate.

With reference to FIG. 8, during inhalation, gas flows from the baseplate 1 through passage 32 into the manifold inhalation entry chamber 33 where it combines with Fresh Gas being delivered through fitting 24 and Fresh Gas port 49. The gas mixture travels upward through the internal passage in valve seat 10i where it lifts disc valve 11i of its seat allowing gas to discharge into manifold inhalation exit chamber 41. From there it passes through passage 34 into passage 35 and into the inhalation hose 18 through fitting 17.

Prior art valves can be difficult for some patients to operate, particularly small patients with small tidal volumes. For example patients with volumes of less than 100 ml more particularly less than 80 ml, particularly less than 70 ml, particularly less than 60 ml, may find it difficult to operate currently available valves. In this embodiment the valve discs 11i and 11e are made of material of the thickness in the range of 0.5 to 1.5 mm, more particularly 0.8 to 1.2 mm, more particularly in this embodiment 1 mm. In this embodiment, the material is plastics, and particularly in this embodiment it is polypropylene. Applicants have found that these valves work with a range of patients including small patients, including small animals.

Figure 10:
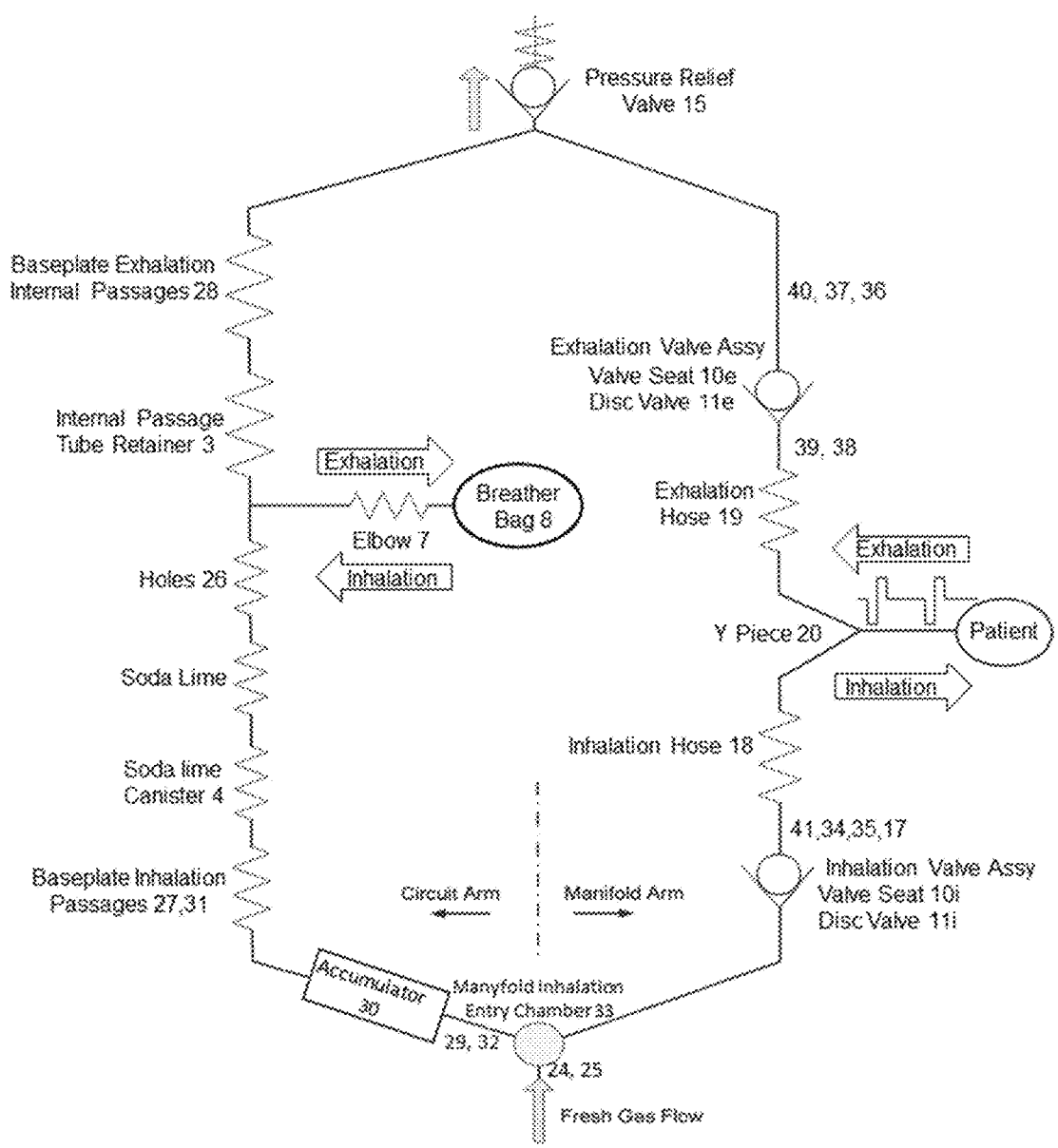
FIG. 10 is a circuit model for a Re-Breather circuit which may be implemented by the apparatus of FIG. 3.

A flow diagram for this Re-Breather circuit is shown in FIG. 10 which identifies all the major elements of this circuit. This circuit is excited by the breathing of the patient. Typically the patient inhales for a period of 1 second. Immediately following this the patient exhales for a period of 1 second which is followed by an end expiratory pause of 4 seconds before the cycle repeats itself.

During inhalation gas flows through the circuit in an anticlockwise direction (the exhalation valve prevents movement in the clockwise direction) from the breather bag 8 to the patient. The gas delivered to the patient is a mixture of the gas contained in the breather bag 8 and the circuit elements between the breather bag 8 and the patient and the Fresh Gas being delivered from the vaporiser. Inhalation draws the gas in the breather bag 8 down through the soda lime in soda lime canister 4 where the $CO_2$ is removed by the soda lime.

During exhalation, gas flows through the circuit in an anticlockwise direction from the patient to the breather bag 8. Some of this gas is expelled and released to the atmosphere through the pressure relief valve 14.

During the end expiratory pause, Fresh Gas continues to be delivered to the circuit from the vaporiser. This Fresh Gas can flow either clockwise or anticlockwise through the circuit.

The Re-Breathing circuit shown in FIGS. 3 to 8 is fundamentally different to previous Re-Breather circuits in that there is a conservation arrangement, in this example being an accumulator 30 positioned immediately adjacent the inhalation valve assembly 10i and 11i and between the inhalation valve assembly 10i and 11i and the soda lime canister 4 and/or the breathing bag 8. In conventional Re-Breather circuits the soda lime canister 4 and/or breather bag 8 is close coupled to the inhalation valve assembly 10i and 11i.

Details of the accumulator are shown in FIG. 9.

The reservoir consists of the accumulator 30, soda lime canister 4, breathing bag 8, internal passages 27, 31, 7, 3, 28, 42 and 15. The reservoir or gas is defined is that gas residing in the reservoir at the end of the inhalation phase.

The function of the accumulator 30 is to store the Fresh Gas entering the circuit arm during the exhalation phase and the end expiratory pause phase and reduce mixing with the contents of the reservoir or the reservoir gas. During the inhalation phase, Fresh Gas stored in the accumulator 30 is drawn into the inhalation hose 18. As a consequence, a slug of Fresh Gas minimally diluted from that delivered by the vaporiser will be delivered to the patient with the minimum of delay—essentially the time taken for the slug of Fresh Gas to be transported the length of the inhalation tube 18.

The accumulator serves two functions. Firstly it has a geometry that prevents mixing of the Fresh Gas with the existing contents of the accumulator. Secondly it stores the Fresh Gas and minimises migration of the Fresh Gas into areas of the reservoir downstream of the accumulator where it would be diluted with the reservoir gas.

The first function is fulfilled by providing a series of long parallel passages 30, 30-2, 30-3, 30-4, 30-5, 30-6 of small invariant cross sectional area through which the Fresh Gas must flow before it can reach the elements downstream of the accumulator, i.e. the soda lime container 4, the breather bag 8 and the internal plumbing. The small cross sectional area of passages 30, 30-2, 30-3, 30-4, 30-5 and 30-6 (compared to the cross sectional flow areas in the soda lime canister and the breather bag) means that lower concentration reservoir gas residing at the interface between the Fresh Gas and the reservoir gas must diffuse a significant distance up these passages before it can affect any significant reduction in the concentration of the Fresh Gas. As the rate of diffusion is slow, the Fresh Gas is preserved minimally diluted by the lower concentration gas residing in the circuit arm.

Furthermore the long passages of uniform cross sectional flow areas creates minimal flow disturbances and minimal turbulent mixing at the interface between the Fresh Gas and the reservoir gas.

The second function is fulfilled by having several long passages such that their combined volume is greater than the tidal volume of the patient. Satisfying this requirement allows the Fresh Gas flow rate to be increased to that of the patient's tidal volume flow rate while ensuring that all the Fresh Gas delivered during the exhalation phase and the end expiratory pause phase will be stored entirely within the accumulator. During the inhalation phase only the undiluted Fresh Gas residing in the accumulator 30 will be sucked into the inhalation hose 18. Consequently the contents of the inlet end of the inhalation hose 18 will be Fresh Gas at the concentration being delivered by the vaporiser.

Thus by increasing the Fresh Gas flow rate to that of the patient's tidal volume flow rate very rapid changes in anaesthetic concentration can be delivered to the patient. Immediately Fresh Gas with an increased anaesthetic concentration is delivered to the Re-Breather circuit it is stored in accumulator 30 and transferred in the subsequent cycle to the inhalation hose 18. If the Fresh Gas flow rate is equal to the patient's tidal volume flow rate, only Fresh Gas at the new anaesthetic concentration is delivered to the inhalation hose 18. The only delay seen by the patient is the delay required for the Fresh Gas to travel along the length of the inhalation hose 18.

As it is physically difficult to provide an accumulator with a volume equal to the tidal volume of the largest patients some compromise is necessary. As discussed previously conventional Re-Breather circuits are normally only used on patients weighing over 10 kg whose tidal volume is typically 100 ml. It is generally difficult to provide a Re-Breather circuit with an accumulator volume this large. Typically accumulator volumes of 50 ml (the tidal volume of a 5 kg animal) can be provided without any adverse impact on the size of the Re-Breather circuit. In the event the accumulator volume is set at 50 ml and the Fresh Gas flow rate is set to the tidal volume flow rate, a 5 kg animal attached to this Re-Breather circuit will always have the inhalation hose charged with anaesthetic gas at the concentration of the Fresh Gas. The same will occur with all animals smaller than 5 kg. For animals with a tidal volume greater than 50 ml there will be some dilution of the gas drawn into the inhalation tube. However, even with 10 kg animals the dilution will be small as the following example illustrates.

Consider the case of a 10 kg animal with a tidal volume of 100 ml and a Fresh Gas flow rate equal to the tidal volume flow rate i.e. 1000 ml/min (tidal volume of 100 ml and a respiratory rate of 10 breaths per minute). Assume the flow resistance of the manifold arm is 3 times that of the circuit arm.

During the end expiratory pause phase lasting 4 seconds, 50 ml of Fresh Gas will be delivered to the circuit arm and 16.7 ml to the manifold arm (flow down each arm will be inversely proportional to the flow resistance of the arms). During the exhalation phase of duration 1 second, the inhalation valve 10*i* and 11*i* is closed so that all the Fresh Gas is delivered to the circuit arm—i.e. 16.7 ml. During these two phases a total of 66.7 ml of Fresh Gas has been delivered to the circuit arm completely filling the accumulator and pushing 16.7 ml into the reservoir downstream of the accumulator where it is diluted by mixing with the reservoir gas. During the one second inhalation phase all the Fresh Gas delivered to the Re-Breather circuit during this phase will be delivered to the inhalation hose 18 (i.e. 16.7 ml) as will the entire contents of the accumulator 30 (50 ml) and 33.4 ml from the reservoir. The latter will consist of a mixture of Fresh Gas (16.7 ml) and reservoir gas (16.7 ml). At the end of the inhalation phase the entry portion of the inhalation hose 18 will be occupied by 100 ml of undiluted Fresh Gas and 16.7 ml of reservoir gas. Even in the worst case where the reservoir gas had zero anaesthetic concentration, the average concentration of the gas delivered during the inhalation phase would be 85.6% that of the Fresh Gas concentration.

Volume of the accumulator may be varied and in other embodiments and is not limited to 50 ml. It may be greater than 100 ml, for example. It also may be other volumes between 20 ml and 100 ml, or any other volume.

The effect of this embodiment on the dynamic response of the Re-Breather circuit is shown in FIG. 16 which compares the response of a traditional Re-Breather circuit (i.e. one that functions in accordance with the simple model) to a Re-Breather circuit incorporating an accumulator in accordance with the invention. Both systems have a 5 kg animal with a tidal volume of 50 ml attached and the Fresh Gas flow rate has been adjusted to the animal's tidal volume flow rate (i.e. 50 ml/breath). The accumulator has a volume of 50 ml. The Re-Breather circuit in accordance with the invention is fitted with a small diameter inhalation hose (12 mm ID) while the traditional Re-Breather circuits are fitted with conventional 22 mm ID inhalation hose. The smaller hose diameter is responsible for the reduced delay experienced before the anaesthetic concentration at the patient first starts to rise as a result of a step change in the Fresh Gas anaesthetic concentration. Unlike a conventional Re-Breather system, the dynamic response is unaffected by the amount of anaesthetic absorbed by the patient.

In the event the Fresh Gas flow rate is lower than the tidal volume flow rate, the volume of Fresh Gas stored in the accumulator will be less than the tidal volume and during inhalation the deficit will be made up with gas from the reservoir, which will be mixed with, and dilute, the Fresh Gas. The response will still be much faster than for a conventional system without the accumulator but the concentration of the gas delivered to the patient will be lower. In the event the ratio of the Fresh Gas flow rate to the tidal volume flow rate is v, then the concentration of gas being delivered to the patient will be:

$$[Patient]=(1-v)[R]+v[FG]$$

Figure 20:
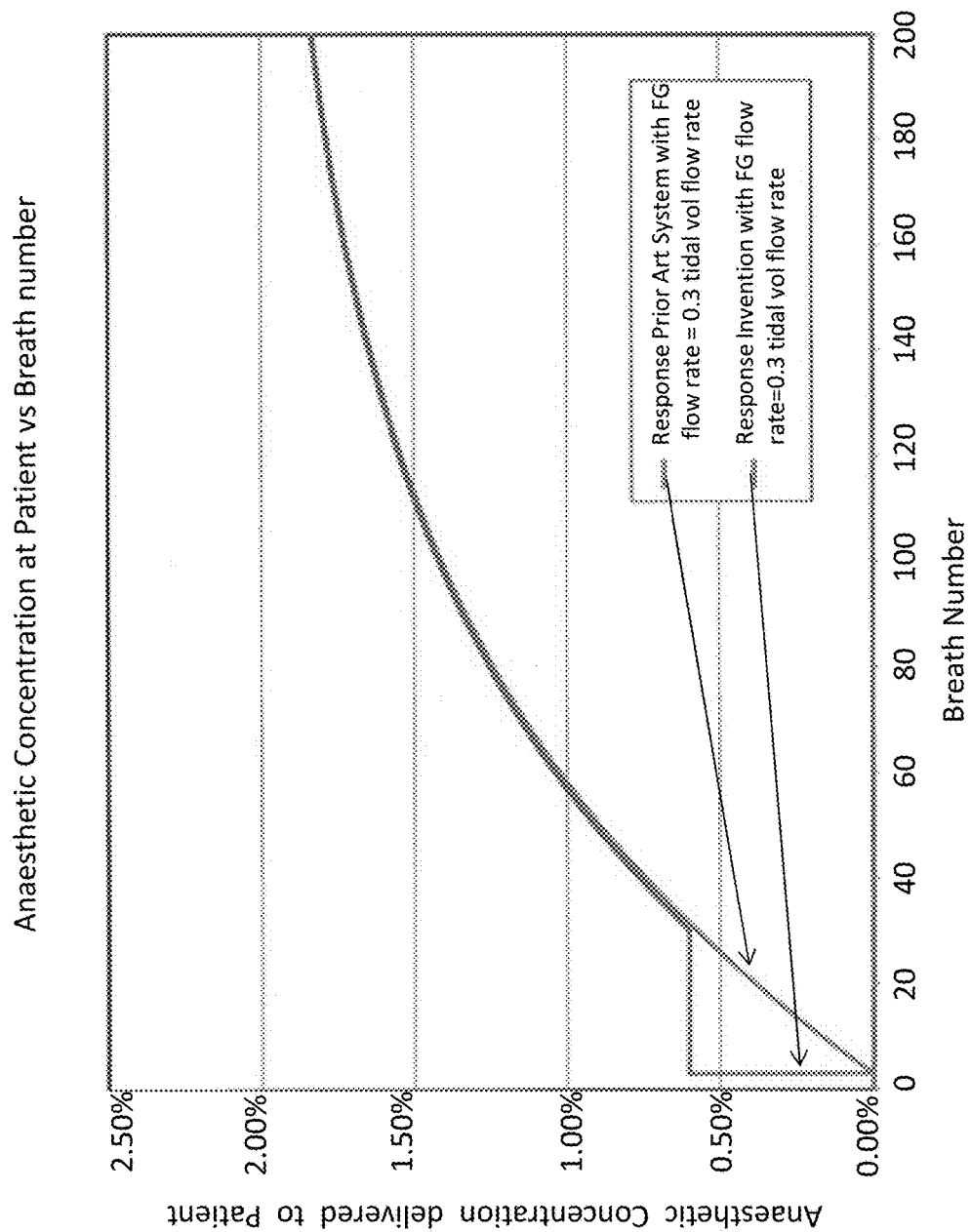
FIGS. 20 and 21 show the response of an apparatus in accordance with an embodiment of the present invention to a step change in anaesthetic concentration of the Fresh Gas with that of a prior art Re-Breather circuit when the Fresh Gas flow rate is less than the patients tidal volume flow rate.

The response seen by the patient when v=0.3 is shown in FIG. 20. In this case the Fresh Gas concentration was 2% and initial reservoir concentration was 0%. When the Fresh Gas has traveled down the inhalation tube to the patient there will be a step change in the concentration seen by the patient to 0.3[FG] or in this case 0.6%. This concentration will remain steady for a short while and thereafter slowly rise. This rise is caused by the anaesthetic returned to the exhalation hose by the patient during exhalation being delivered to the Reservoir where it starts to increase the anaesthetic concentration of the Reservoir. As the anaesthetic concentration of the reservoir gas increases there is less dilution of the incoming Fresh Gas.

The anaesthetist can choose any level of response between this and the response shown in FIG. 16 where the Fresh Gas Flow rate was increased so that it was equal to the tidal volume flow rate. In the latter case the anaesthetic not absorbed by the patient will be returned to the reservoir via the exhalation hose and over time the reservoir anaesthetic concentration will rise.

Figure 21:
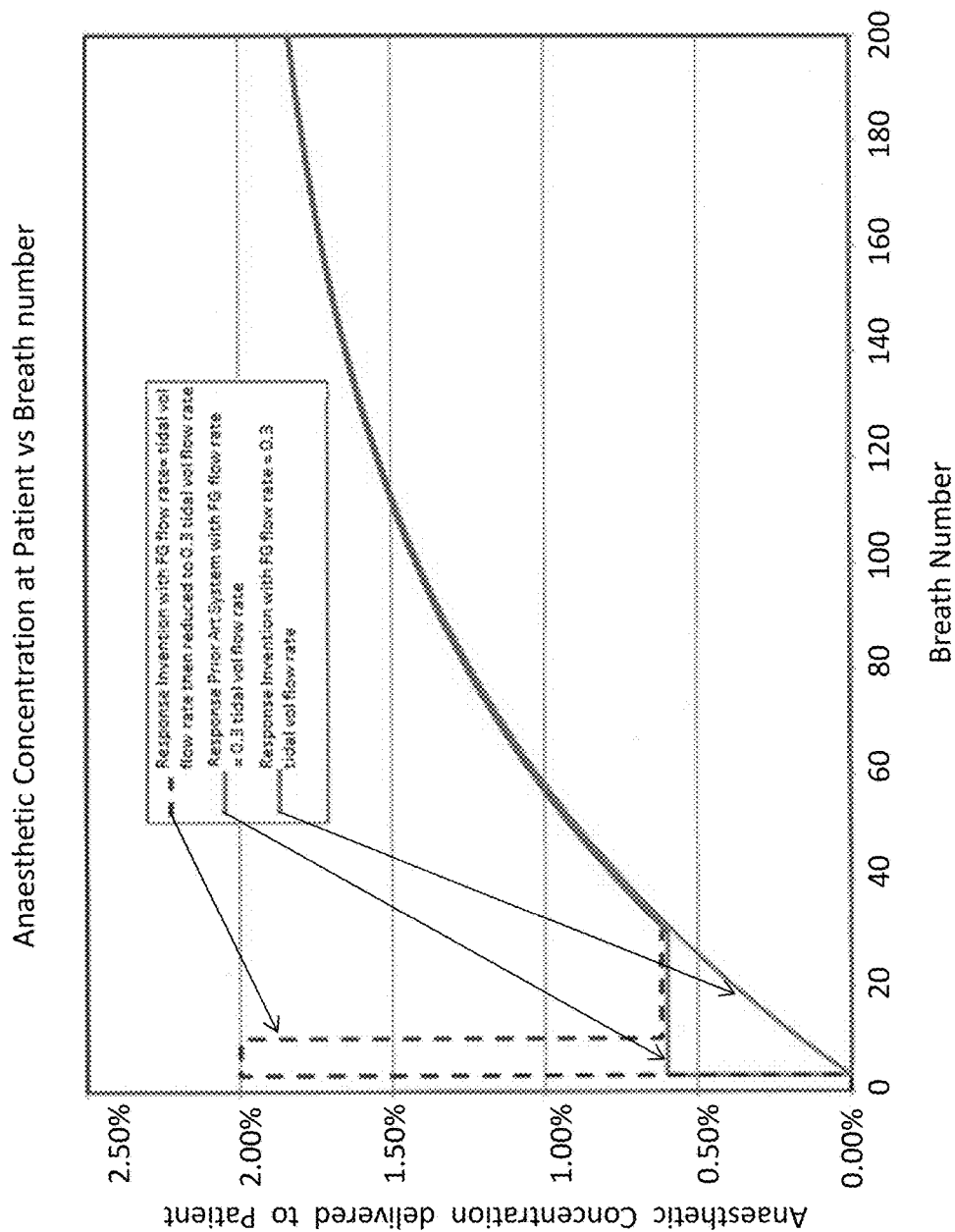

If, however, the Fresh Gas flow rate is reduced before the reservoir concentration has an opportunity to increase, then any reduction in Fresh Gas flow rate will be accompanied by a rapid fall in the anaesthetic concentration delivered to the patient. In FIG. 21 the dashed line shows the case where the initial Fresh Gas flow rate is set to equal that of the tidal volume flow rate and shortly afterwards reduced to 0.3 of the tidal volume flow rate.

By this method the anaesthetist can by varying the Fresh Gas flow rate deliver a very fast increase in the anaesthetic concentration seen by the patient and also a very fast decrease in the anaesthetic concentration seen by the patient. Similar results can be obtained by leaving the Fresh Gas flow rate constant and varying the anaesthetic concentration of the Fresh Gas. These fast response rates are exactly what is required when animals start to wake up in the middle of an operation and must be quickly re-sedated.

It should be appreciated that the response curves shown FIGS. 20 and 21 for the systems according to this embodiment are calculated results assuming no mixing of the Fresh Gas and the reservoir gas. In reality there will be a degree of mixing and consequently the response will be a little slower than that depicted in FIGS. 20 and 21.

The ability to affect rapid decreases in anaesthetic concentration at the patient is another feature of this embodiment. Just as the prior art systems have a slow response to a step increase in the Fresh Gas concentration, they also have a slow response to a step decrease in the Fresh Gas concentration. Consider a Re-Breather circuit in equilibrium delivering an anaesthetic concentration of 2%. If the Fresh Gas concentration is step changed to zero, it will take a long time before the anaesthetic concentration at the patient approaches zero because the Fresh Gas will first need to progressively dilute the reservoir gas down to zero anaesthetic concentration. The larger the reservoir volume and the smaller the Fresh Gas flow the longer it will take to reduce the reservoir anaesthetic concentration to zero.

The Re-Breather system according to this embodiment has three major advantages when used on small animals. Firstly the anaesthetic concentration delivered to the patient is independent of the anaesthetic uptake of the patient. In the event the Re-Breather circuit has an accumulator volume equal or greater than the patient's tidal volume, it will deliver anaesthetic at the Fresh Gas concentration to the patient, irrespective of the level of anaesthetic uptake by the patient. By way of comparison the anaesthetic concentration delivered to the patient by traditional systems is dependent on the anaesthetic uptake of the patient. Only in the impossible event where the patient absorbs no anaesthetic ($\beta$=0) does the anaesthetic concentration delivered to the patient equal that of the Fresh Gas. In the event the patient absorbs all the delivered anaesthetic ($\beta$=1) only anaesthetic at 50% of the Fresh Gas concentration is delivered to the patient.

Secondly, the speed at which changes in the Fresh Gas concentration are delivered to the patient is at least an order of magnitude faster than that of traditional systems. In the current example the Re-Breather circuit delivers anaesthetic at the Fresh Gas concentration to the patient in 3.4 breaths compared to the traditional system that requires over 100 breaths (30 times faster) and which can only achieve this in the impossible event that the patient absorbs none of the anaesthetic.

In a real world situation, where the patient absorbs anaesthetic, the Fresh Gas concentration on conventional systems must be increased over that delivered by the invention if the patient is to be supplied with anaesthetic at the same concentration as that supplied by the invention. In the patient in FIG. 16 absorbs all the anaesthetic delivered ($\beta$=1), then the Fresh Gas concentration must be increased to 4% or double that required by the invention. The response of a traditional system supplied with anaesthetic at 4% concentration is shown in FIG. 16. Even after doubling the Fresh Gas concentration, the traditional system still requires 47 breaths to deliver anaesthetic to the patient at 95% of the concentration supplied by the invention; more than 13 times slower than the invention.

Finally, the embodiment consumes less anaesthetic than the traditional system. In practice the elevated level of anaesthetic delivered to the patient will sedate the patient and the patient's uptake of anaesthetic will reduce). At this stage both the Fresh Gas concentration and flow rate will be reduced to conserve anaesthetic and $O_2$ and maintain anaesthetic concentration at safe levels. During that period when the Fresh Gas flow rate and concentration are temporarily increased to re-sedate a waking patient, the traditional system consumes far more anaesthetic than does the system of this embodiment of the invention to effect the same result. In the current example the traditional system consumes up to twice, depending on the anaesthetic uptake of the patient, that of the embodiment to achieve the same outcome. The explanation for this higher anaesthetic usage is that the traditional system discharges gas through the pressure relief valve to the atmosphere at the same concentration that is being delivered to the patient while the invention discharges gas to the atmosphere at a much reduced concentration to that being supplied to the patient.

In order to minimise the consumption of anaesthetic gas the pressure relief valve 14 is located at a position in the Re-Breather circuit where the anaesthetic concentration is lowest. In Re-Breather circuits of embodiments of the current invention this occurs adjacent (upstream of) the exhalation valve 10e and 11e. This location is remote from the accumulator 30 which means minimal, if any, Fresh Gas will migrate to this position and the gas being delivered to the pressure relief valve from the exhalation hose 19 has had its anaesthetic concentration depleted by the uptake of anaesthetic by the patient.

The anaesthetic apparatus of this invention is not useful only for small animals. Embodiments of the apparatus increase efficiency of an anaesthetic circuit for all patients, human or animal, large or small. The dynamic response of the circuit is increased. For large patients, this means that relatively low flow of anaesthetic can be used as compared with prior art systems. This results in an increased efficiency, low cost and reduction of pollution.

The accumulator 30 may take many forms. FIGS. 11 and 12 show one such alternative which is amenable to manufacture by plastic injection moulding or casting. In this arrangement the accumulator consists of a series of passages 43 (consisting of 43-1, 43-2, 43-3, 43-4, 43-5, 43-6, 43-7, 43-8) formed between closely spaced adjacent ribs in baseplate 44. Passages 43 are enclosed by a plate (not shown) attached to the face 45 of baseplate 44. One end of the passages 43 is located adjacent the entry to the inhalation valve assembly 46 and the Fresh Gas entry 47. The other end is located adjacent baseplate entry holes 48 that provide access to the soda lime container. During the exhalation phase and the end expiratory pause phase Fresh Gas flows from the Fresh Gas entry 47 into the accumulator passages 43 pushing before it the low anaesthetic concentration reservoir gases into the soda lime container through the baseplate entry holes 48.

The accumulator may take other forms. For example, helically wound channels that wind around each other and provide very long pathways to limit dilution, could be utilised. Other forms could be utilised.

Conservation of Fresh Gas adjacent to an inhalation part of an anaesthetic circuit may be achieved in other ways than using an accumulator such as described above. For example, a valve may be placed at the inhalation port to enable a bag or other container to be filled with Fresh Gas available for use on inhalation. Other ways may be used to conserve Fresh Gas at the inhalation portion of the circuit. Such a valve arrangement could prevent dilution of the Fresh Gas all together i.e. stop it mixing completely and act to conserve the Fresh Gas completely.

The above embodiments have particular advantage with smaller patients such as small animals. Embodiments of the invention are not limited to use with small animals, however, and may also be used with small and adult humans, and adult animals.

In the above embodiments, the soda lime canister is arranged so that flow is unidirectional from the holes 26 to the ports 27 in the system. Also, the gas flow passes from the inside (centre) of the canister to the outside. The Applicants believe that this is an efficient way of utilising the carbon dioxide scrubber in the container. The ports 27, are placed toward the exhalation side of the system.

Figure 18:
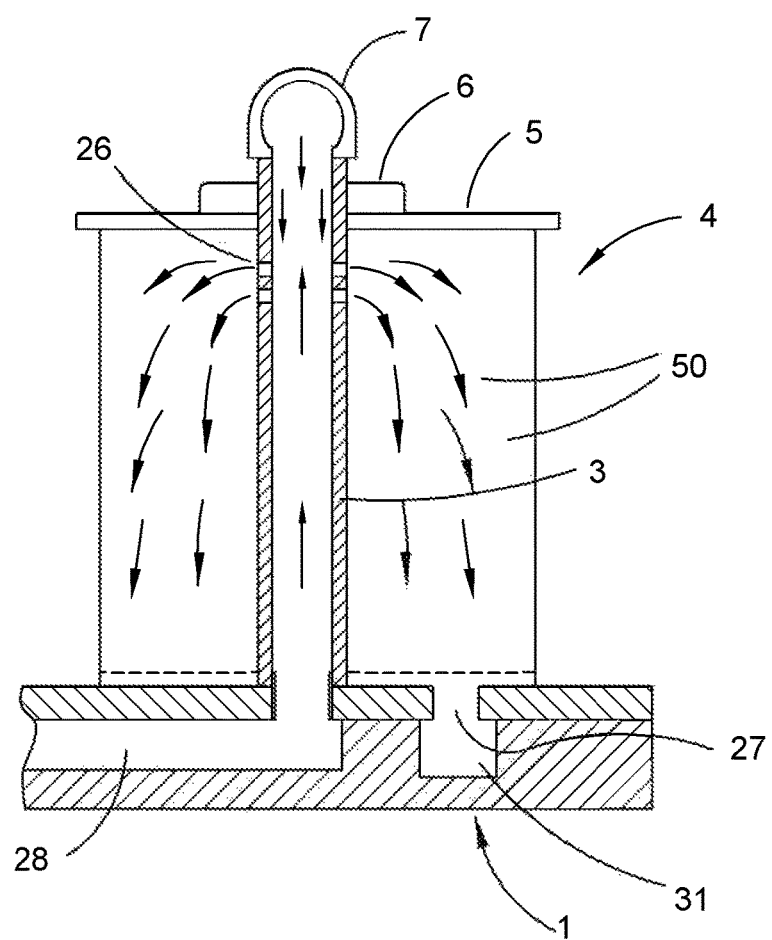
FIG. 18 is a longitudinal cross-sectional diagram through a scrubber canister of an anaesthetic apparatus in accordance with an embodiment of the present invention, mounted on a baseplate.

FIG. 18 is a schematic cross-section through a soda lime canister 4 showing by the arrows 50 the direction of exhaled air through the soda lime canister. Soda lime canister 4 in this case is designed to provide a large surface area for absorption of the carbon dioxide. The large surface area provides lower resistance to flow and therefore allows gas to back up into the accumulator rather than to resist the accumulation of gas.

A chemical strip may be provided in the soda lime canister to show when the soda lime is exhausted. The soda lime will tend to exhaust in layers from the top downwards, so the strip (not shown) will extend downwardly the length of the canister. Alternatively, sensors (e.g. impedance sensors) may be used to sense changes in resistance/impedance of the soda lime to determine when it is exhausted.

Closed Re-Breather circuits are advantageous for smaller patients for a number of reasons, including that the small patients are less likely to be cooled, as they are not losing warm air which is being replaced by cool air (as in a non-Re-Breather circuit). Some of the warm air remains in the circuit. Warming may be enhanced by providing heating in the circuit. In one embodiment the tubing may be heating (see applicant's co-pending patent application relating to heated tubing Australian Provisional Patent Application No. 2011903770 filing date 14 Sep. 2011). In an embodiment the plate 1 may also include heating element(s) to heat the air as it flows through.

Various sensors may be placed throughout the circuit to determine gas flow, temperatures, carbon dioxide amount. The sensors may upload data to a processing device such as a computer monitoring patient health.

The positioning of the components in the system of this embodiment is such as to facilitate the conservation effect of the conservation arrangement 200. Ports 27, as discussed above, are positioned away from the inhalation side of the opposite end of the accumulator and towards the exhalation side. The "pop off" valve port 42 is also positioned next to the exhalation side.

The above embodiments disclose a circuit which is particularly designed to facilitate slowing of mixing of Fresh Gas with gas in the rest of the circuit. It is not essential to use components of the circuit together, however. Some components may be used in other types of circuits with different components. For example, the accumulator may be used with different components than disclosed above (e.g. conventional inhalation and exhalation valves, conventional soda lime containers, and other conventional components) and still provide a significant slowing or mixing effect.

The accumulator may be of any other geometry that slows gas mixing, and is not limited to the geometries discussed in the above embodiments.

In the above embodiment, the inhalation and exhalation lines may be conventional 22 ml diameter lines. In other embodiments, at least the inhalation line may be of lesser diameter, and may be of, for example, 10 to 16 mm, or 12 or 15 mm in diameter. Having a smaller inhalation line may be effective for patients with smaller tidal volumes. The exhalation line may also be smaller.

The above described embodiments relate to anaesthetic apparatus. An apparatus in accordance with embodiment of the present invention is not limited to delivering anaesthetic it may be used to deliver other fluids. For example, it could be used to deliver any medication to the lung or mucosal lining, for example, oxygen for the treatment of ulcers, nitric oxide, or any other medication.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of stated features but not to preclude the presence or addition of further features in various embodiments of the invention.

What is claimed is:

1. An anaesthetic apparatus for use in an anaesthetic re-breather circuit, comprising:
a conservation arrangement having an accumulator arrangement positioned, in use, between an inhalation part of an anaesthetic re-breather circuit and other downstream components of the anaesthetic re-breather circuit, the inhalation part having an inhalation port and a fresh gas inlet, so that, in use, a fresh gas entering the anaesthetic re-breather circuit must flow from the inhalation part through the accumulator arrangement to the other downstream components of the anaesthetic re-breather circuit before being diluted with a gas already contained in the other downstream components of the anaesthetic re-breather circuit, and a gas already contained in the other downstream components of the anaesthetic re-breather circuit must pass through the accumulator arrangement to reach the inhalation part,
wherein the conservation arrangement is arranged to conserve the fresh gas entering the anaesthetic re-breather circuit proximate the inhalation port for delivery undiluted or predominantly undiluted to a patient on inhalation and slow mixing of the fresh gas entering the anaesthetic re-breather circuit with the gas already contained in the anaesthetic re-breather circuit.

2. The anaesthetic apparatus of claim 1, wherein the accumulator arrangement is positioned, in use, immediately adjacent the inhalation port and arranged to accumulate the fresh gas entering the anaesthetic re-breather circuit.

3. The anaesthetic apparatus of claim 2, wherein the accumulator arrangement has a geometry arranged to reduce a flow of the fresh gas away from the inhalation port to reduce mixing of the fresh gas in the accumulator arrangement with the gas already contained in the anaesthetic re-breather circuit.

4. The anaesthetic apparatus of claim 3, wherein the accumulator arrangement comprises an elongate accumulator passage of a smaller cross sectional area as compared with cross sectional areas of passageways in a rest of the anaesthetic re-breather circuit and arranged to have an accumulator volume equal to or greater than one quarter of a breathing tidal volume of a smallest intended patient for which the anaesthetic re-breather circuit is to be used.

5. The anaesthetic apparatus of claim 4, wherein the elongate accumulator passage has a cross sectional area that is 50% or less than that of a minimum cross sectional area in the rest of the anaesthetic re-breather circuit.

6. The anaesthetic apparatus of claim 4, wherein the accumulator arrangement comprises a plurality of the accumulator passages, the plurality of the accumulator passages arranged to receive and accumulate the fresh gas.

7. The anaesthetic apparatus of claim 6, wherein the plurality of the accumulator passages have a combined cross sectional area which is 50% or less than a minimum cross sectional area of the rest of the anaesthetic re-breather circuit.

8. The anaesthetic apparatus of claim 2, wherein the accumulator arrangement has a proximal end arranged to be positioned, in use, proximate the fresh gas inlet of the anaesthetic re-breather circuit to receive and accumulate the fresh gas entering the anaesthetic re-breather circuit, and proximate an inspiration arm of the anaesthetic re-breather circuit to deliver the fresh gas accumulated in the accumulator arrangement directly to the inspiration arm with a minimal dilution, and a distal end having an outlet to the other downstream components of the anaesthetic re-breather circuit.

9. The anaesthetic apparatus of claim 2, wherein the volume of the accumulator arrangement is arranged to be of a same order of magnitude as a tidal volume of a patient to be anaesthetised using the anaesthetic re-breather circuit.

10. The anaesthetic apparatus of claim 1, further comprising a housing mounting the conservation arrangement, and comprising ports and passageways arranged to connect to other components of the anaesthetic apparatus.

11. The anaesthetic apparatus of claim 10, wherein the ports and passageways of the housing are arranged to connect the other components of the anaesthetic apparatus in positions which optimise operation of the conservation arrangement.

12. The anaesthetic apparatus of claim 10, wherein the ports and passageways comprise a pressure relief valve port arranged to connect to a pressure release valve, whereby the pressure release valve port is, in operation, at a position in the anaesthetic re-breather circuit where a concentration of an anaesthetic is lowest.

13. The anaesthetic apparatus of claim 12, further comprising a valve manifold, arranged to mount an exhalation valve so that an outlet of the exhalation valve opens into a port connected to the pressure release valve port.

14. The anaesthetic apparatus of claim 13, wherein, for the valve manifold mounting an inhalation valve, an inlet of the inhalation valve is arranged proximate the fresh gas inlet of the housing.

15. A method of facilitating anaesthesia, comprising:
slowing mixing of fresh gas entering an anaesthetic re-breather circuit with a gas already contained in the anaesthetic re-breather circuit using a conservation arrangement having an accumulator arrangement positioned, in use, between an inhalation part of the anaesthetic re-breather circuit and other downstream components of the anaesthetic re-breather circuit, the inhalation part having an inhalation port and a fresh gas inlet, so that the fresh gas entering the anaesthetic re-breather circuit must flow from the inhalation part through the accumulator arrangement to the other downstream components of the anaesthetic re-breather circuit before being diluted with a gas already contained in the other downstream components of the anaesthetic re-breather circuit, and the gas already contained in the other downstream components of the anaesthetic re-breather circuit must pass through the accumulator arrangement to reach the inhalation part, to thereby conserve the fresh gas entering the anaesthetic re-breather circuit proximate the inhalation port for delivery undiluted or predominantly undiluted to a patient on inhalation.

16. The method of claim 15, wherein slowing mixing of the fresh gas comprises accumulating the fresh gas entering the circuit during an exhalation phase and an exhalation pause in a patient's breathing.

17. The method of claim 16, wherein accumulating comprises accumulating the fresh gas proximate an inspired limb of the anaesthetic re-breather circuit.

18. The method of claim 15, wherein slowing mixing of the fresh gas comprises positioning components of the anaesthetic re-breather circuit to reduce a flow of the fresh gas away from the inhalation part to facilitate damping.

19. An anaesthetic apparatus, arranged for implementation of an anaesthetic re-breather circuit, the anaesthetic apparatus comprising a housing, having a fresh gas port for receiving a fresh gas from a vaporiser, an inhalation port for providing a gas to an inhalation conduit for a patient, an exhalation port for receiving an expired gas from the patient, the anaesthetic apparatus further comprising a container for containing a carbon dioxide absorbent, and a compliant reservoir for absorbing pressure fluctuations within the anaesthetic re-breather circuit, the fresh gas port, the inhalation port, the exhalation port, the carbon dioxide absorbent container and the compliant reservoir being connected by passageways such that they form a circuit through which a gas flows in one direction from the fresh gas port, the inhalation port to the patient, from the exhalation port, to the canister and compliant reservoir and back to the inhalation port, wherein the fresh gas inlet and the inhalation port are proximate one another and wherein the anaesthetic apparatus further comprises an accumulator located downstream of the fresh gas inlet and connected proximate said inhalation port in the circuit whereby the gas in the circuit from the exhalation port canister and compliant reservoir must flow through the accumulator to the inhalation port, the accumulator being arranged to conserve the fresh gas entering the anaesthetic re-breather circuit proximate the inhalation port for delivery undiluted or predominantly undiluted to the patient on inhalation and slow mixing of the fresh gas with the gas in the rest of the circuit.

* * * * *